United States Patent
Fawcett et al.

(10) Patent No.: US 9,470,611 B2
(45) Date of Patent: Oct. 18, 2016

(54) SAMPLE PLATE FOR SLIDING MAGNETIC PARTICLE SEPARATION

(71) Applicant: Gilson, Inc., Middleton, WI (US)

(72) Inventors: Kevin Fawcett, Ridgeway, WI (US); Gregory J. Robinson, Sun Prairie, WI (US); David John Guckenberger, Oconomowoc, WI (US); Scott Berry, Madison, WI (US)

(73) Assignee: Gilson, Inc., Middleton, WI (US)

( * ) Notice: Subject to any disclaimer, the term of this patent is extended or adjusted under 35 U.S.C. 154(b) by 0 days.

(21) Appl. No.: 14/595,985

(22) Filed: Jan. 13, 2015

(65) Prior Publication Data

US 2016/0202156 A1    Jul. 14, 2016

(51) Int. Cl.
B01D 21/00    (2006.01)
G01N 1/38    (2006.01)

(52) U.S. Cl.
CPC ........... G01N 1/38 (2013.01); *G01N 2001/386* (2013.01)

(58) Field of Classification Search
CPC .......................... G01N 33/54326; G01N 1/38
See application file for complete search history.

(56) References Cited

U.S. PATENT DOCUMENTS

| | | | |
|---|---|---|---|
| 3,938,961 A | 2/1976 | Lanier | |
| 4,986,965 A * | 1/1991 | Ushikubo | B01L 3/508 220/737 |
| 6,448,092 B1 | 9/2002 | Tuunanen | |
| 6,921,513 B2 * | 7/2005 | Schubert | B01L 3/5085 422/501 |
| 8,603,416 B2 | 12/2013 | Beebe et al. | |
| 2004/0022677 A1 * | 2/2004 | Wohlstadter | B01L 3/5085 422/52 |
| 2009/0117004 A1 | 5/2009 | Fritchie et al. | |
| 2014/0190894 A1 | 7/2014 | Beebe et al. | |

FOREIGN PATENT DOCUMENTS

| | | |
|---|---|---|
| DE | 3439877 A1 | 10/1984 |
| EP | 1997557 A1 | 12/2008 |
| WO | WO2012/052033 | 4/2012 |

OTHER PUBLICATIONS

Greiner HLA Terasaki multiwell plates, Downloaded from http://www.sigmaaldrich.com/catalog/product/sigma/m5812?lang=en&region=US on Dec. 8, 2014, pp. 1-2.
TempPlate semi-skirted 96-well polypropylene PCR plate, raised sides, natural, Downloaded from http://www.usascientific.com/semi-skirted-96-well-pcr-plate-raised-contoured-sides.aspx on Dec. 5, 2014, pp. 1-2.
96-Well Semi-Skirted Plates, Raised Deck, Downloaded from http://www.thermoscientificbio.com/plastic-consumables/96-well-semi-skirted-plates-raised-deck/ on Dec. 5, 2014.
International Search Report and Written Opinion mailed on Apr. 1, 2016, for International Patent Appl. No. PCT/US2016/012827, 12 pp.

\* cited by examiner

*Primary Examiner* — Jyoti Nagpaul
(74) *Attorney, Agent, or Firm* — Bell & Manning, LLC

(57) ABSTRACT

A sample plate includes a top surface, a plurality of wells, and a plurality of reservoirs. The plurality of wells is mounted to the top surface. Each well includes a well bottom surface and a well wall extending up from the well bottom surface. The plurality of reservoirs is mounted to the top surface. Each reservoir includes a reservoir bottom surface, a reservoir wall extending from a first side of the reservoir bottom surface, and the well wall extending from a second side of the reservoir bottom surface. Each reservoir of the plurality of reservoirs surrounds a corresponding well of the plurality of wells.

22 Claims, 21 Drawing Sheets

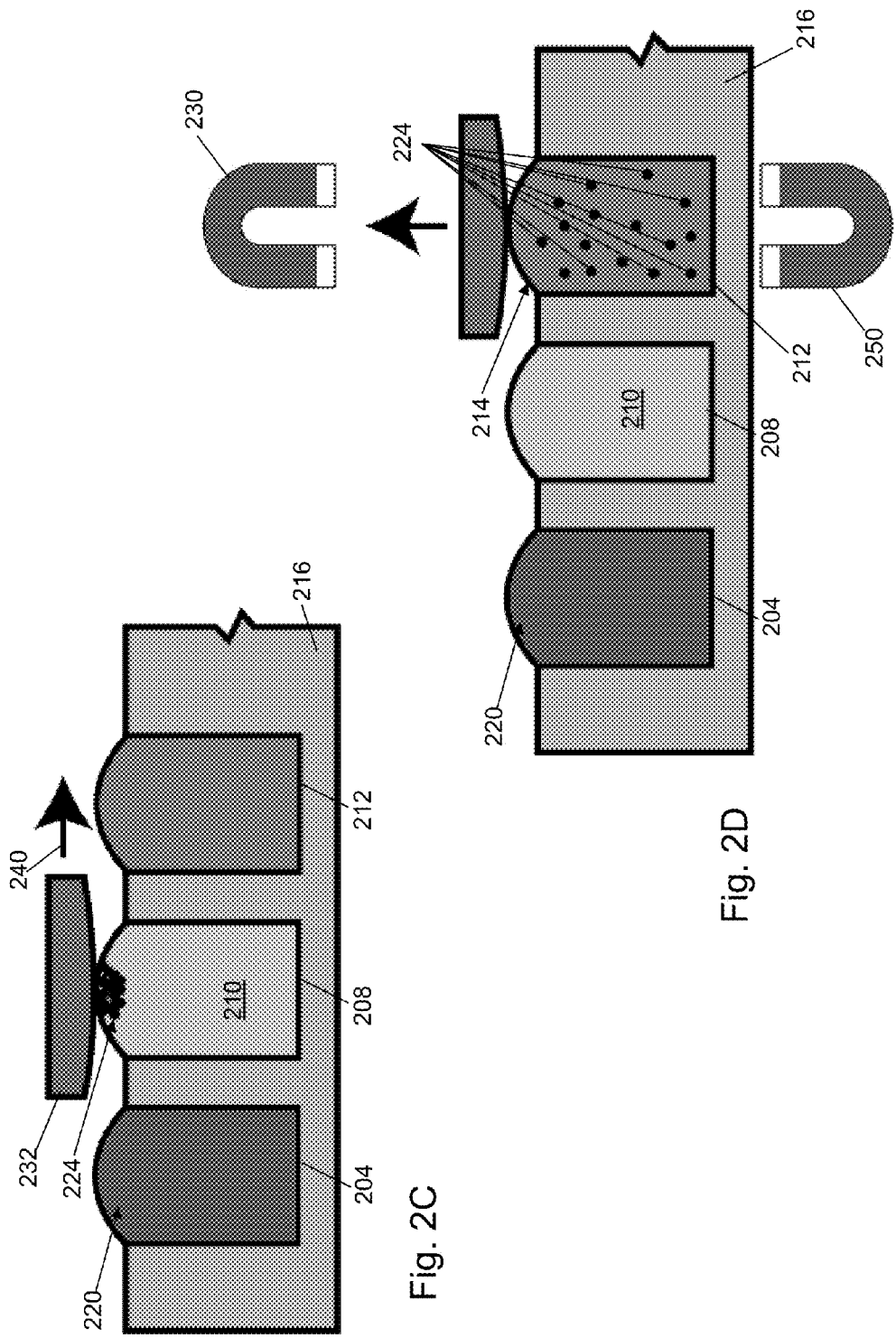

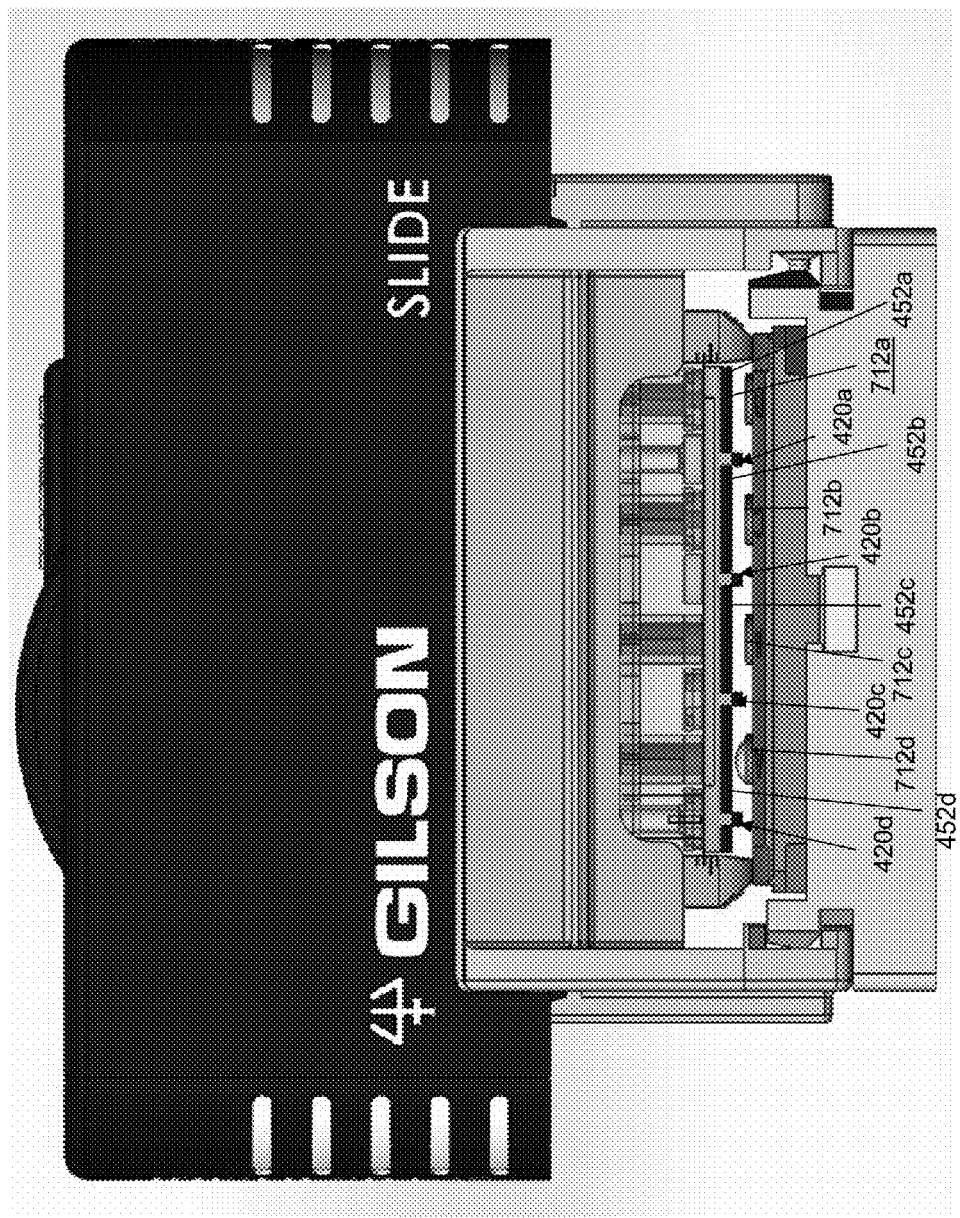

SAMPLE PLATE FOR SLIDING MAGNETIC PARTICLE SEPARATION

BACKGROUND

Processing of liquid samples to isolate desired components from other components that may be present in the liquid samples is ubiquitous in a variety of fields. For example, DNA sequencing can involve first lysing cells containing the target DNA to form a lysate, a complex mixture of the desired nucleic acids and other components such as cellular debris and lysing reagents. Before the desired nucleic acids can be amplified, detected and quantified, they must be isolated from these other components.

SUMMARY

In an example embodiment, a sample plate is provided. The sample plate includes, but is not limited to, a top surface, a plurality of wells, and a plurality of reservoirs. The plurality of wells is mounted to the top surface. Each well includes a well bottom surface and a well wall extending up from the well bottom surface. The plurality of reservoirs is mounted to the top surface. Each reservoir includes, but is not limited to, a reservoir bottom surface, a reservoir wall extending from a first side of the reservoir bottom surface, and the well wall extending from a second side of the reservoir bottom surface. Each reservoir of the plurality of reservoirs surrounds a corresponding well of the plurality of wells.

In another example embodiment, a sample processing system is provided. The sample processing system includes, but is not limited to, a first base, the sample plate, and a sliding head. The first base includes, but is not limited to, an upper surface. The sample plate is mounted to the upper surface. The sliding head is mounted to the first base to translate over the sample plate in a translation direction. The sliding head includes, but is not limited to, a housing that includes a second base, a magnet mounted in the housing to extend through the second base, and an adapter mounted to the second base.

Other principal features and advantages of the disclosure will become apparent to those skilled in the art upon review of the following drawings, the detailed description, and the appended claims.

Illustrative embodiments of the disclosure will hereafter be described with reference to the accompanying drawings, wherein like numerals denote like elements.

BRIEF DESCRIPTION OF THE DRAWINGS

FIGS. 2A-2D depict a method of isolation performed by the sample processing system of FIG. 1A.

FIG. 8 depicts a front view of a sample processing system in accordance with a second illustrative embodiment.

DETAILED DESCRIPTION

Figure 1A:
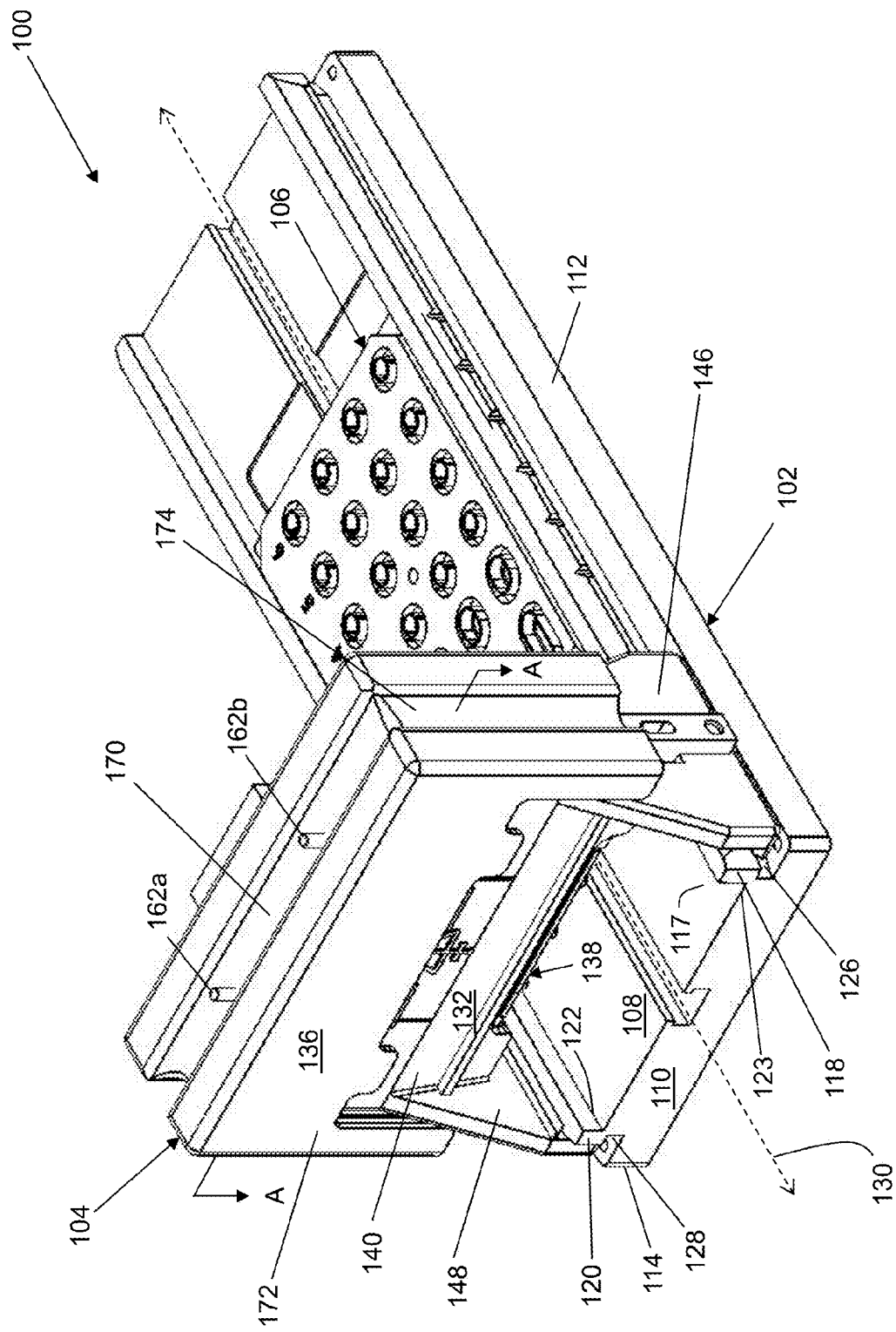
FIG. 1A depicts a perspective view of a sample processing system in accordance with an illustrative embodiment.
Figure 1B:
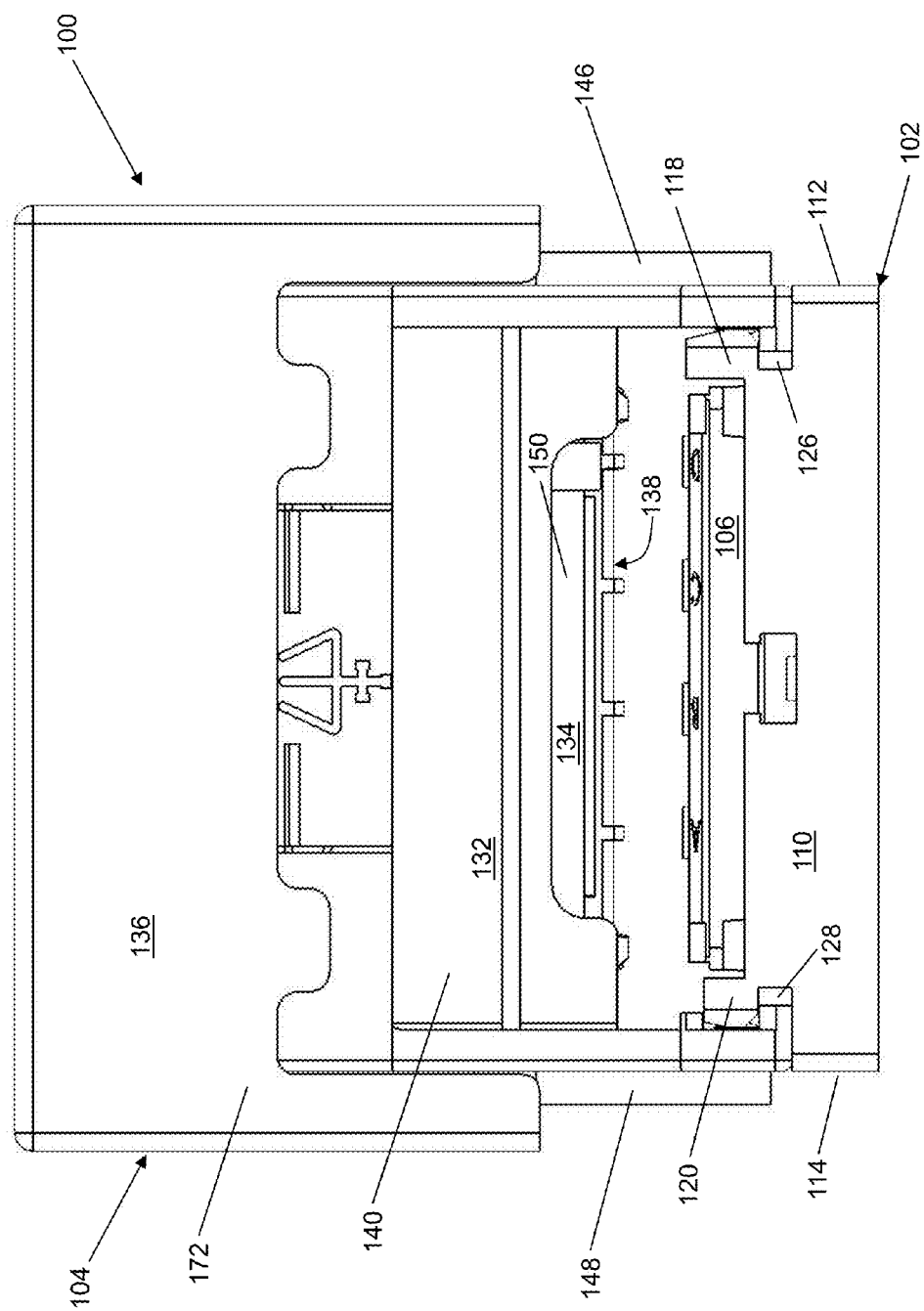
FIG. 1B depicts a front view of the sample processing system of FIG. 1A.
Figure 1C:
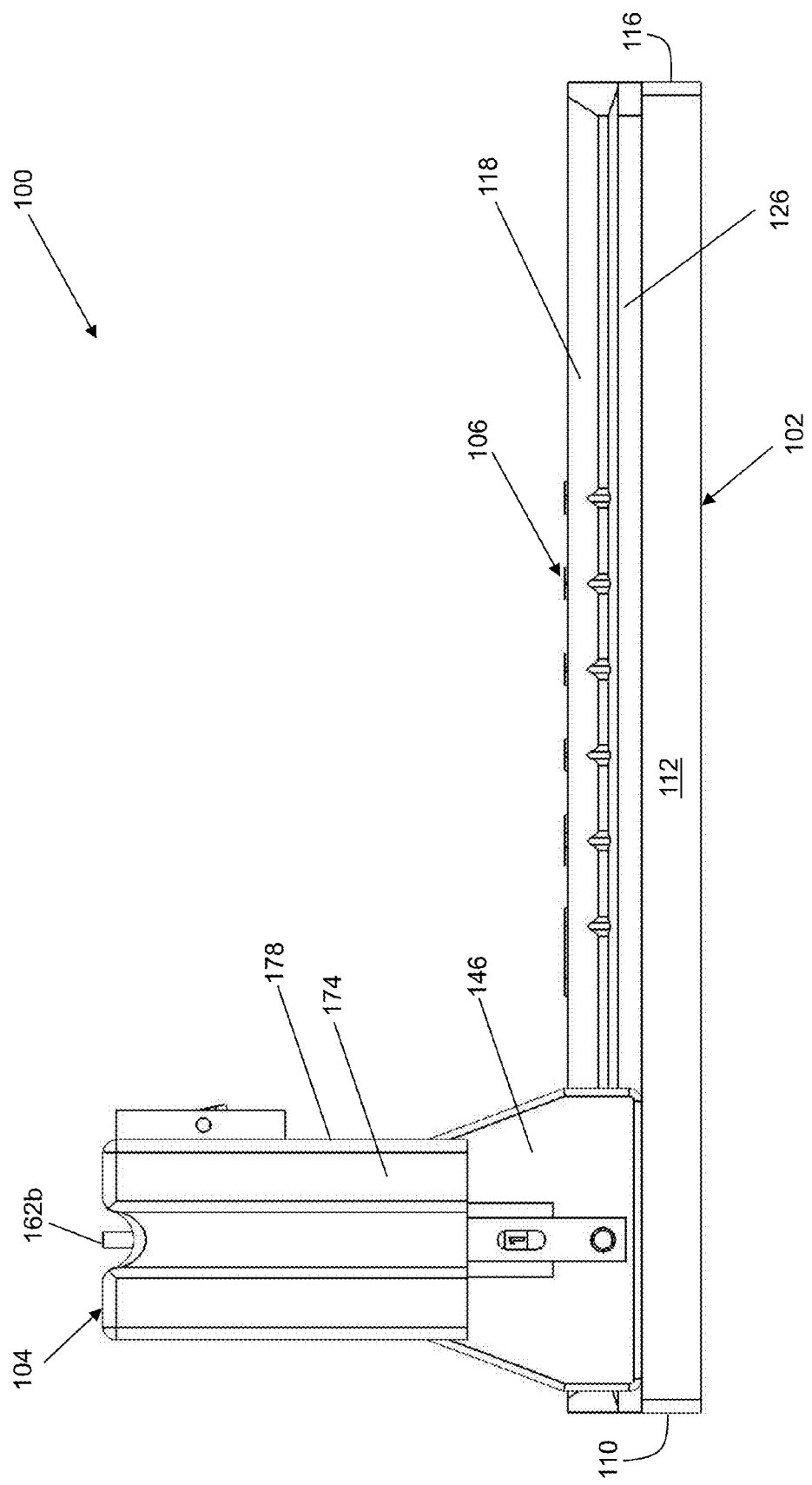
FIG. 1C depicts a right side view of the sample processing system of FIG. 1A.
Figure 1D:
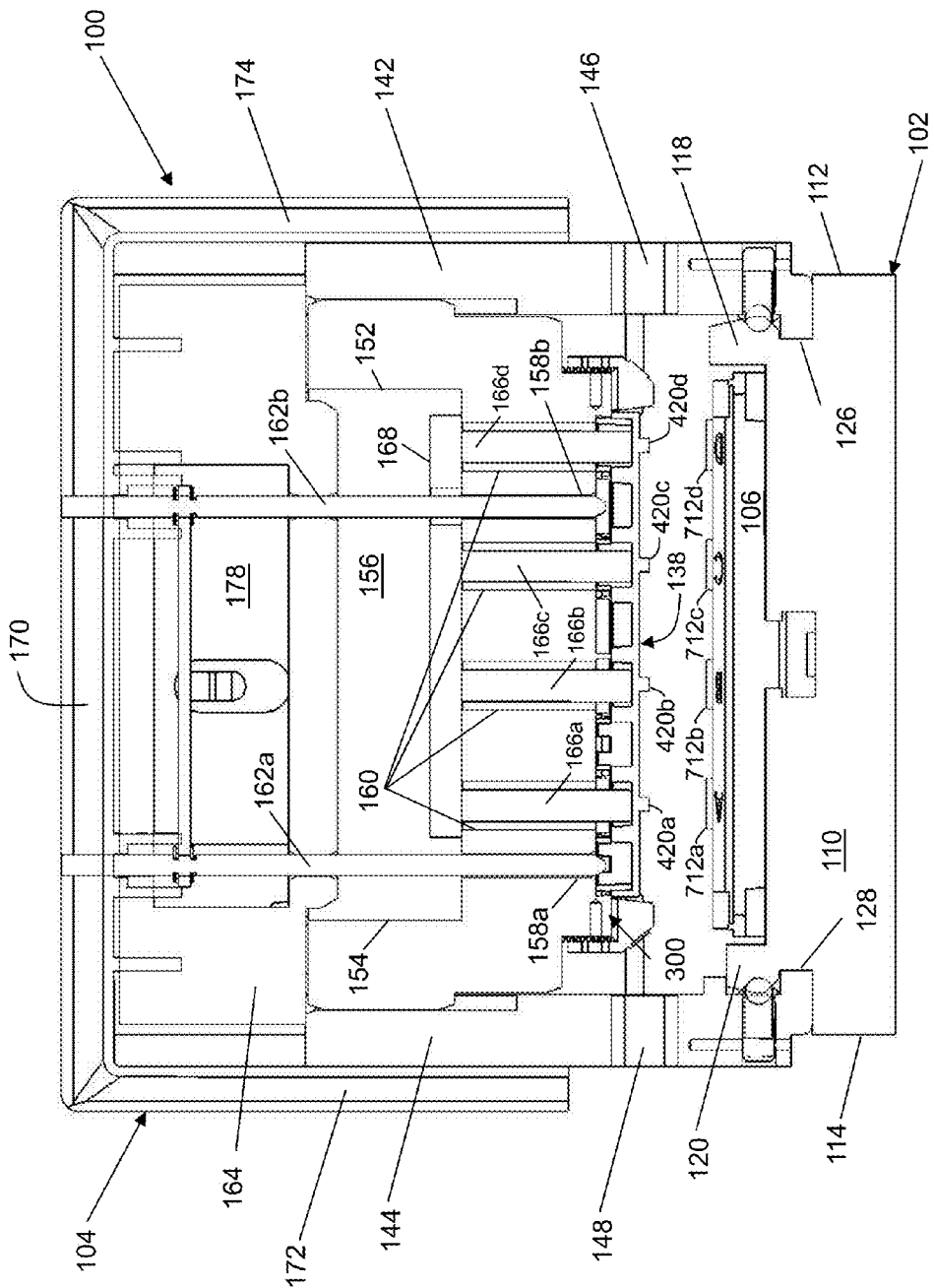
FIG. 1D depicts a front, cross-sectional view of the sample processing system of FIG. 1A.

With reference to FIGS. 1A-D, views of a sample processing system 100 are shown in accordance with an illustrative embodiment. With reference to FIG. 1A, a perspective view of sample processing system 100 is shown. With reference to FIG. 1B, a front view of sample processing system 100 is shown. With reference to FIG. 1C, a right side view of sample processing system 100 is shown. With reference to FIG. 1D, a front, cross-sectional view of sample processing system 100 is shown, taken along section A-A. Sample processing system 100 may include additional, fewer, or different components.

Sample processing system 100 may be used to isolate target analytes from liquid samples in which target analytes have been bound to a solid substrate (e.g., paramagnetic beads). Sample processing system 100 may include any device that isolates target analytes by moving (e.g., via a magnet) solid substrate and bound target analytes from the liquid samples to one or more distinct liquid-containing zones (e.g., liquid droplets or liquid-filled wells) formed in the surface of a substrate. Sample processing system 100 may be used to process any type of liquid samples (e.g., biological samples) in order to isolate a variety of types of target analytes (e.g., proteins, nucleic acids, cells, etc.) from other components which may be present in the liquid samples (e.g., solvent, blood, urine, sputum, plants, cells, etc.). As such, sample processing system 100 may be used as a platform for DNA or protein purification, cell separation, etc. Such techniques are widely used in basic laboratory research, drug discovery, disease diagnosis and monitoring, etc.

Figure 2A:
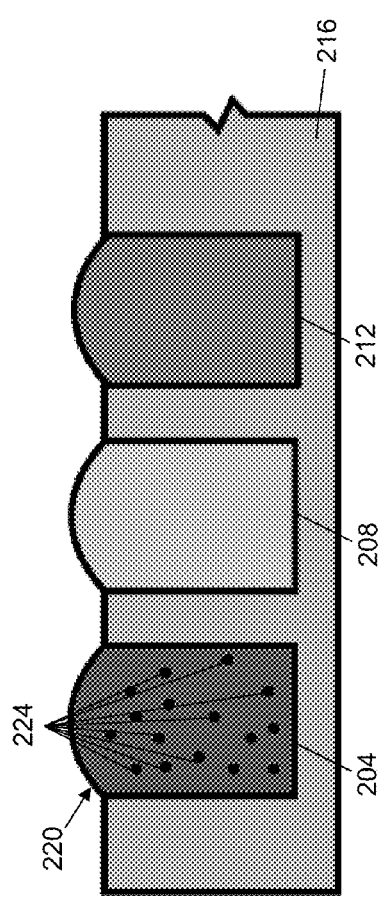

An illustrative method of isolation performed by sample processing system 100 is schematically illustrated in FIGS. 2A-2D. As shown in FIG. 2A, a first well 204, a second well 208, and a third well 212 may be mounted to a surface of a substrate 216. As used herein, the term "mount" includes join, unite, connect, couple, associate, insert, hang, hold, affix, attach, fasten, bind, paste, secure, bolt, screw, rivet, solder, weld, glue, form over, form in, layer, mold, rest on, rest against, abut, and other like terms. The phrases "mounted on", "mounted to", and equivalent phrases indicate any interior or exterior portion of the element referenced. These phrases also encompass direct mounting (in which the referenced elements are in direct contact) and indirect mounting (in which the referenced elements are not in direct contact, but are connected through an intermediate element). Elements referenced as mounted to each other herein may further be integrally formed together, for example, using a molding or thermoforming process as understood by a person of skill in the art. As a result, elements described herein as being mounted to each other need not be discrete structural elements. The elements may be mounted permanently, removably, or releasably unless specified otherwise.

A liquid sample 220 may be deposited in first well 204. Liquid sample 220 may include a variety of components, including target analytes (e.g., cells) bound to a plurality of particles 224. Particles 224 may be magnetic, paramagnetic, or ferromagnetic.

Figure 2B:
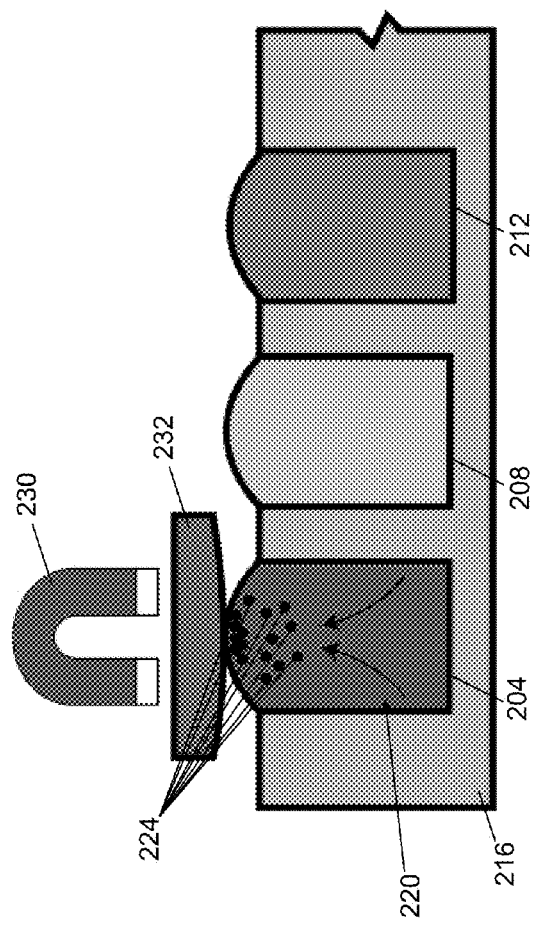

In a first step as depicted in FIG. 2B, a magnet 230 mounted to an adapter 232 is positioned over first well 204 such that a magnetic force from magnet 230 attracts and holds a plurality of particles 224 bound with target analytes to a bottom surface of adapter 232. Use of directional terms, such as top, bottom, right, left, front, back, etc. are merely intended to facilitate reference to various surfaces that form components of the devices referenced herein and are not intended to be limiting in any manner.

In a second step as depicted in FIG. 2C, adapter 232 with magnet 230 is translated along in a direction shown by an axis 240 until magnet 230 is positioned over second well 208. A liquid 210 may be deposited in second well 208. Liquid 210 may include a processing reagent (e.g., stain) for modifying target analytes. The plurality of particles 224 bound with target analytes may be immersed in liquid 210 of second well 208 when magnet 230 is positioned over second well 208. Other components of liquid sample 220 that were not bound to the plurality of particles 224 may remain within first well 204.

In a third step as depicted in FIG. 2D, adapter 232 with magnet 230 is further translated along axis 240 until magnet 230 is positioned over third well 212. A liquid 214 may be deposited in third well 212. Liquid 214 may include a wash solvent. The plurality of particles 224 bound with target analytes may be immersed in liquid 214 of third well 212 when magnet 230 is positioned over third well 212. Release of magnet 230 or application of a repulsive magnetic force releases the plurality of particles 224 bound with target analytes, which subsequently disperse within liquid 214 of third well 212. Dispersion of the plurality of particles 224 may be facilitated by a second magnet 250 positioned below substrate 216. Liquid 214, including the plurality of particles 224 with the now processed and isolated target analytes (e.g., stained cells), may be removed for further analysis.

With reference back to FIGS. 1A-D, sample processing system 100 may include a base 102, a sliding head 104, and a sample plate 106. Sample processing system 100 may be an automated system or used manually using a hand of a user as understood by a person of skill in the art. Adapter 232 may be mounted to sliding head 104 without touching adapter 232 to avoid contamination, which may occur even when a user wears gloves. Base 102 may include a base plate 108, a front wall 110, a right side wall 112, a left side wall 114, and a back wall 116. Base plate 108 includes a top surface 117. Base plate 108 may include a first rail 118 extending from top surface 117 along a right edge 123 of base plate 108 and a second rail 120 extending from top surface 117 along a left edge 122 of base plate 108. Base 102 may include a first elongated channel 126 between right side wall 112 and first rail 118 and a second elongated channel 128 between left side wall 114 and second rail 120. Base 102 may include a recess (not shown) formed in top surface 117 which is configured to receive and support sample plate 106 in a fixed position.

Base plate 108, its walls 110, 112, 114, 116 and its rails 118, 120 may be formed as a single piece. Base 102 provides a support structure for sliding head 104 and sample plate 106. Sliding head 104 may slide back and forth over sample plate 106 along a longitudinal axis 130 via rails 118, 120 and elongated channels 126, 128 while sample plate 106 is fixed in position on base 102.

Sliding head 104 may include an outer housing 132, an inner housing 134, a cover 136, and an adapter 138. Adapter 138 is an illustrative embodiment of adapter 232 of FIGS. 2A-2D. Outer housing 132 may be mounted to base 102. Outer housing 132 may include a front wall 140, a right side wall 142, a left side wall 144, and a back wall (not shown) which define an interior configured to receive and enclose inner housing 134. Outer housing 132 may include a right leg 146 extending from right side wall 142 and a left leg 148 extending from left side wall 144. An end of right leg 146 may be configured to engage with first rail 118 and first elongated channel 126 of base 102. An end of left leg 148 may be configured to engage with second rail 120 and second elongated channel 128. As such, sliding head 104 may slide back and forth on base 102 in the direction of longitudinal axis 130. The walls 140, 142, 144 (and the back wall) and legs 146, 148 of outer housing 132 may be formed as a single piece.

Inner housing 134 may be mounted within the interior of outer housing 132. Inner housing 134 may include a bottom plate 300 (shown with reference to FIG. 3A), a front wall 150, a right side wall 152, a left side wall 154, and a back wall 156 that define an interior space. Bottom plate 300 and its walls 150, 152, 154, 156 may be formed as a single piece.

Inner housing 134 may include a plurality of channels 158a, 158b, and 160 formed within the interior space. Channels 158a and 158b may be configured to receive a first ridge member 162a and a second rigid member 162b, respectively, and to align first and second rigid member 162a and 162b approximately perpendicular to a plane of base 102 that may be defined by top surface 117 of base plate 108. First and second rigid members 162a and 162b may be mounted to a spring ejector system 164 mounted to inner housing 134, outer housing 132, and cover 136. Spring ejector system 164 may be configured to allow first and second rigid members 162a and 162b to move downwardly within channels 158a and 158b, respectively, when a user pushes downwardly on cover 136. In an automated system, the ejector system may be moved under electronic controls automatically. The force exerted on adapter 138 when first and second rigid members 162a and 162b make contact with recesses 414a and 414g (shown with reference to FIG. 4) of adapter 138 detaches adapter 138 from inner housing 134. A variety of rigid members may be used, e.g., rods, bars, pins, etc.

Each channel of the channels 160 of inner housing 134 may be configured to receive a magnet of a plurality of magnets 166a-d and to align the plurality of magnets 166a-d approximately perpendicular to sample plate 106. The plurality of magnets 166a-d may be mounted to a bar 168 mounted within inner housing 134. The plurality of magnets 166a-d may be mounted as a linear array. The plurality of magnets 166a-d may be mounted such that their centers pass approximately over the centers of wells 712a-d of sample plate 106 when translating over sample plate 106. In a manual system, the plurality of magnets 166a-d may be free floating. In an automated system, the plurality of magnets 166a-d may be moved under electronic controls automatically.

Figure 3A:
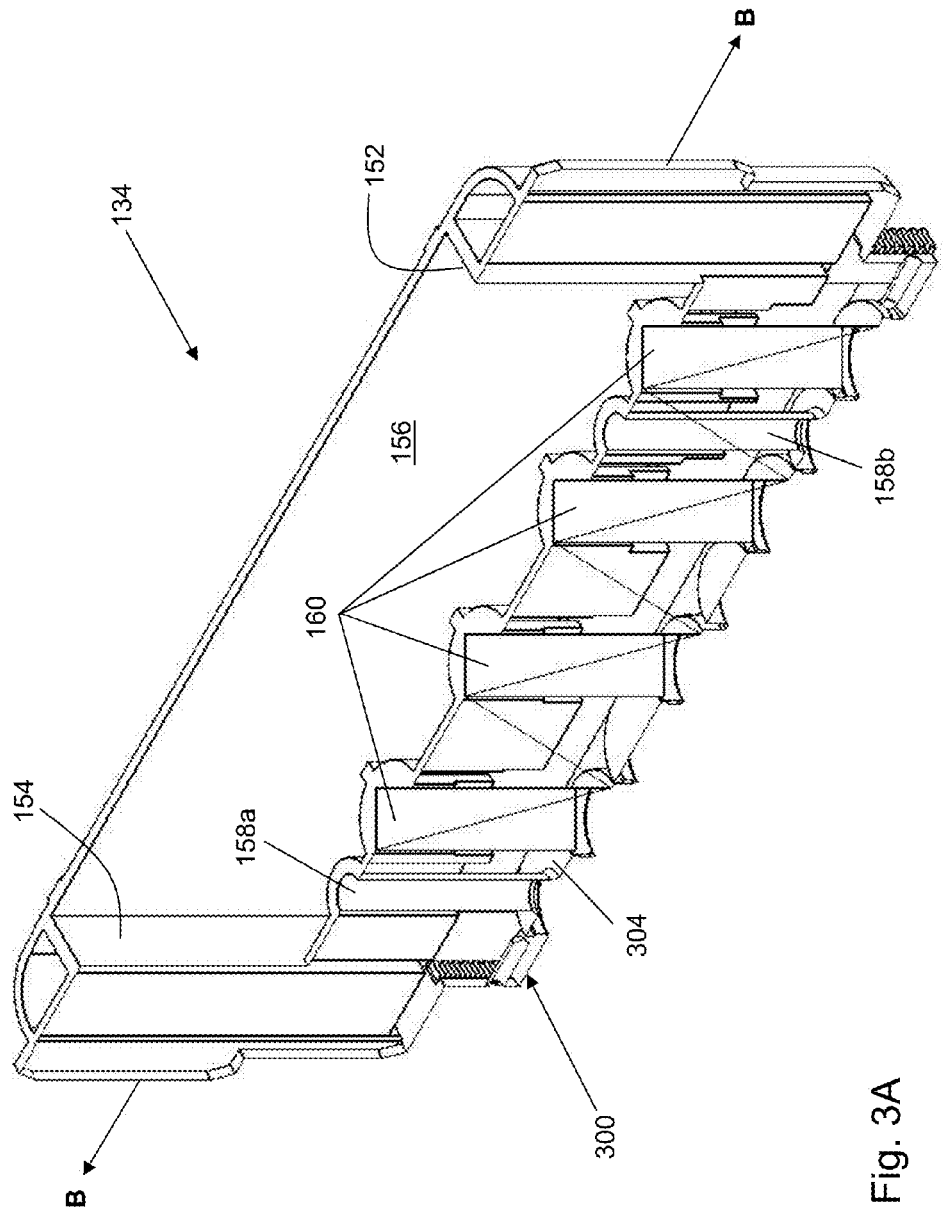
FIG. 3A depicts a perspective, cross-sectional view of an inner housing of the sample processing system of FIG. 1A.
Figure 3B:
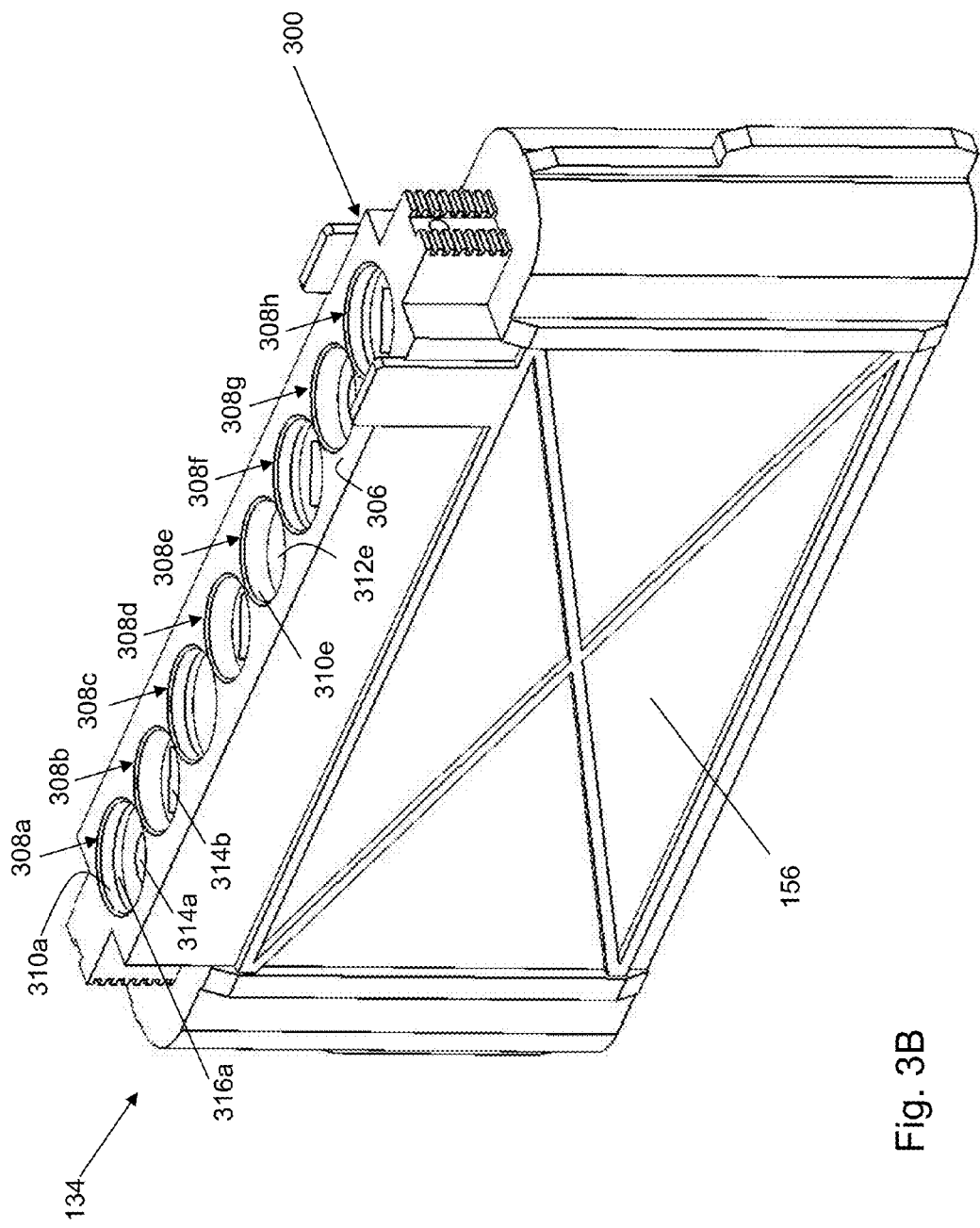
FIG. 3B depicts a bottom, perspective view of the inner housing of FIG. 3A.

With reference to FIG. 3A, a perspective, cross-sectional view of inner housing 134 is shown taken along section A-A of FIG. 1A. With reference to FIG. 3B, a bottom, perspective view of inner housing 134 is shown (i.e., in which inner housing 134 has been rotated 180° about axis B). Bottom plate 300 of inner housing 134 has a top surface 304 and a bottom surface 306. Bottom plate 300 may include a plurality of recesses 308a-h formed in bottom plate 300. Each recess of the plurality of recesses 308a-h has side walls that extend from bottom surface 306 towards top surface 304 and an inner surface. A side wall 310e and an inner surface 312e of recess 308e are labeled for illustration. Some recesses of the plurality of recesses 308a-h may include an aperture formed through bottom plate 300 to allow an end of first or second rigid members 162a, b or an end of one of the plurality of magnets 166 to pass through the inner surface of the recess into the interior of inner housing 134. An aperture 314a of recess 308a is labeled for illustration. Aperture 314a may be shaped and sized to allow an end of first rigid member 162a to pass through the inner surface and into the interior of inner housing 134. Recess 308g may be similarly configured to allow an end of second rigid member 162b to pass through the inner surface and into the interior of inner housing 134. An aperture 314b of recess 308b is labeled. Aperture 314b may be shaped and sized to allow an end of a magnet of the plurality of magnets 166 to pass through the inner surface. Recesses 308d, 308f, and 308h may be configured similar to recess 308b. Recesses 308c and 308e may be blank recesses which receive neither a magnet nor a rigid member.

Adapter 138 may be mounted to bottom plate 300 of inner housing 134. One or more of the plurality of recesses 308a-h of bottom plate 300 may include a groove formed in side walls configured to receive tabs (e.g., 506a-d shown with reference to FIG. 5) on projections (e.g., 500a-d shown with reference to FIG. 5) of adapter 138 to mount adapter 138 to bottom plate 300. A groove 316a formed in side walls 310a of recess 308a is labeled for illustration. Recesses 308c, 308f, and 308h may be similarly configured.

With continuing reference to FIGS. 1A-D, cover 136 of sliding head 104 may include a top plate 170, a front wall 172, a right side wall 174, a left side wall 176, and a back wall 178. Top plate 170 and walls 172, 174, 176, 178 define an interior configured to receive and enclose spring ejector system 164, inner housing 134, and outer housing 132. Top plate 170 and its walls 172, 174, 176, 178 may be formed as a single piece.

Figure 4A:
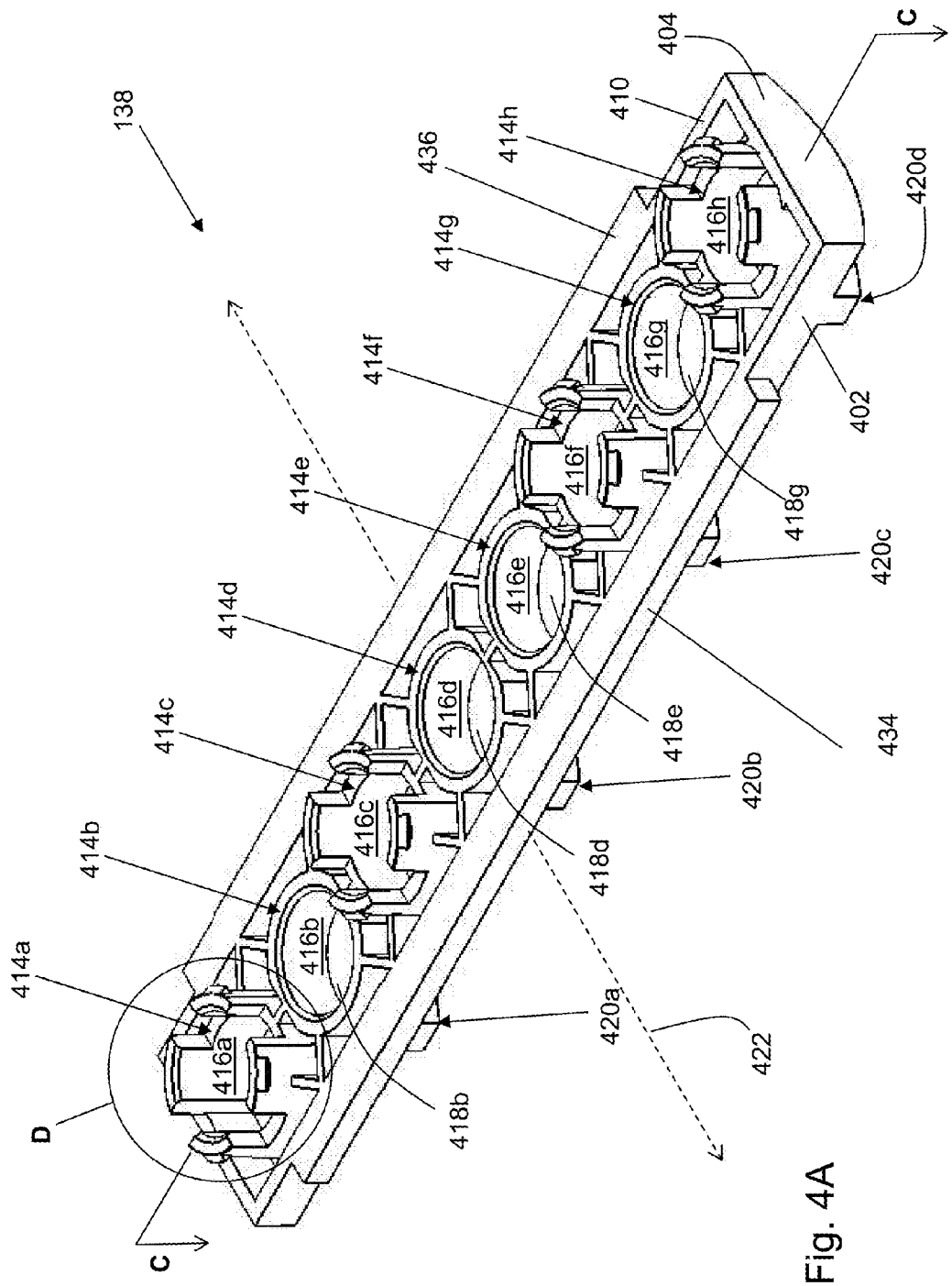
FIG. 4A depicts a top, perspective view of an adapter of the sample processing system of FIG. 1A.
Figure 4B:
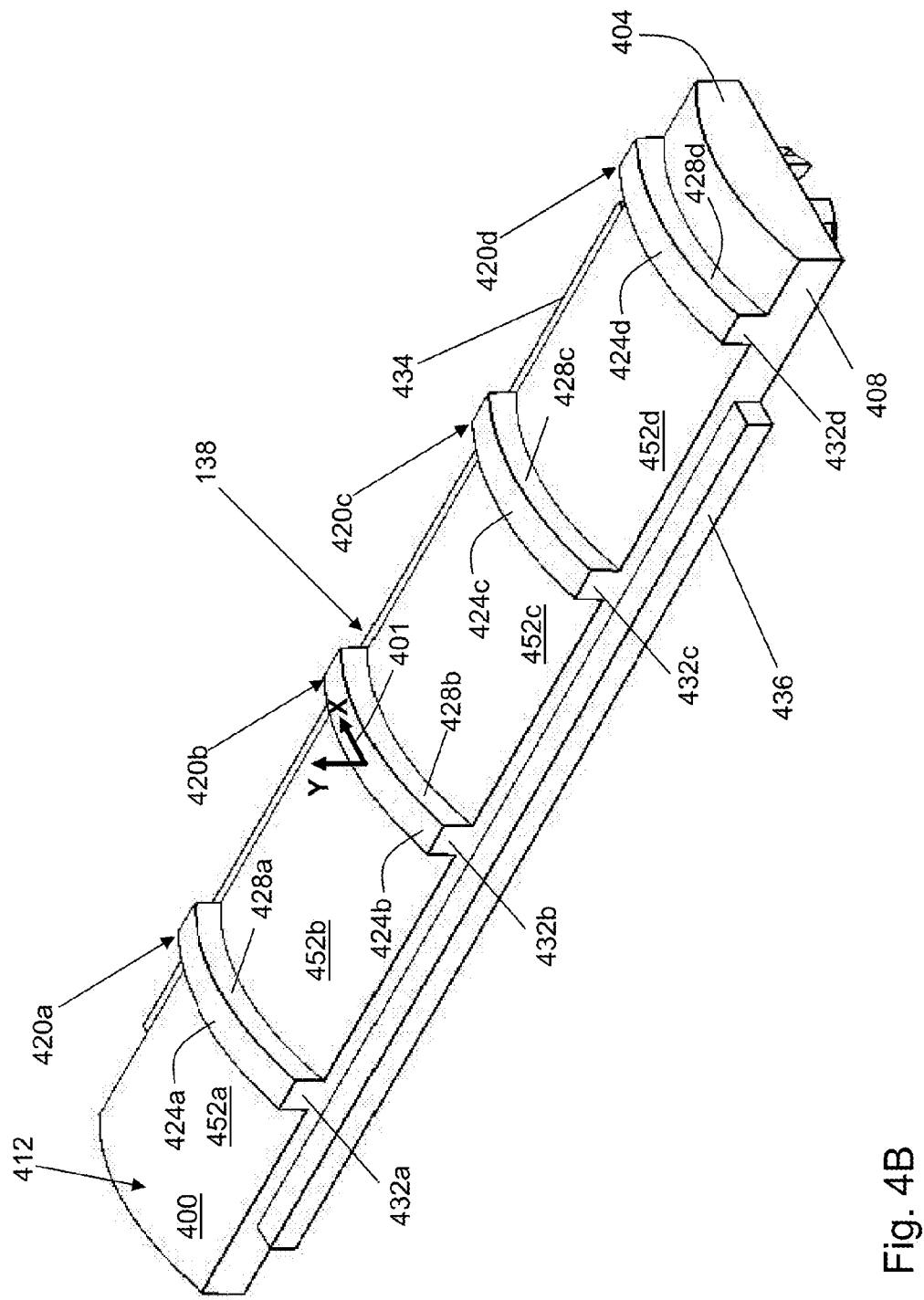
FIG. 4B depicts a bottom, perspective view of the adapter of FIG. 4A.
Figure 4C:
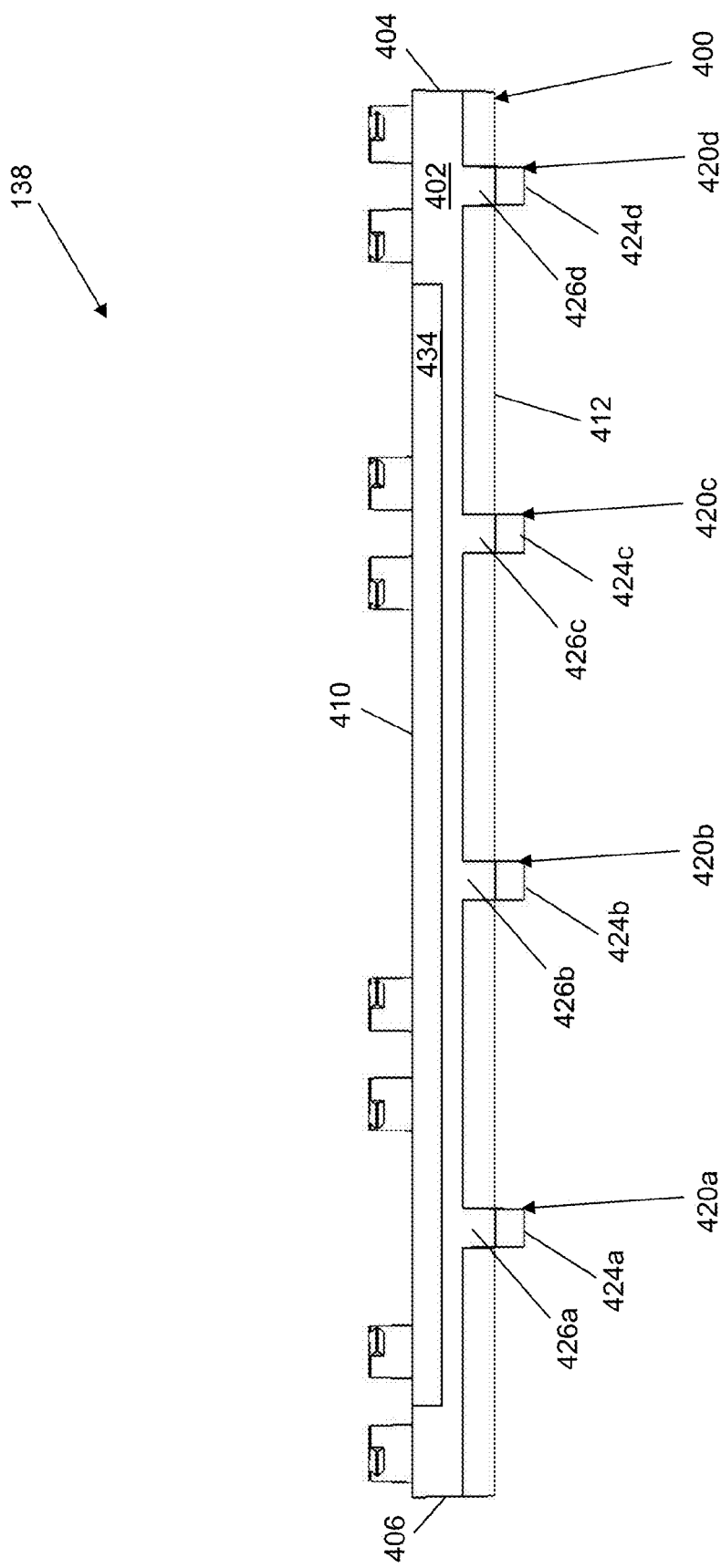
FIG. 4C depicts a front view of the adapter of FIG. 4A.
Figure 4D:
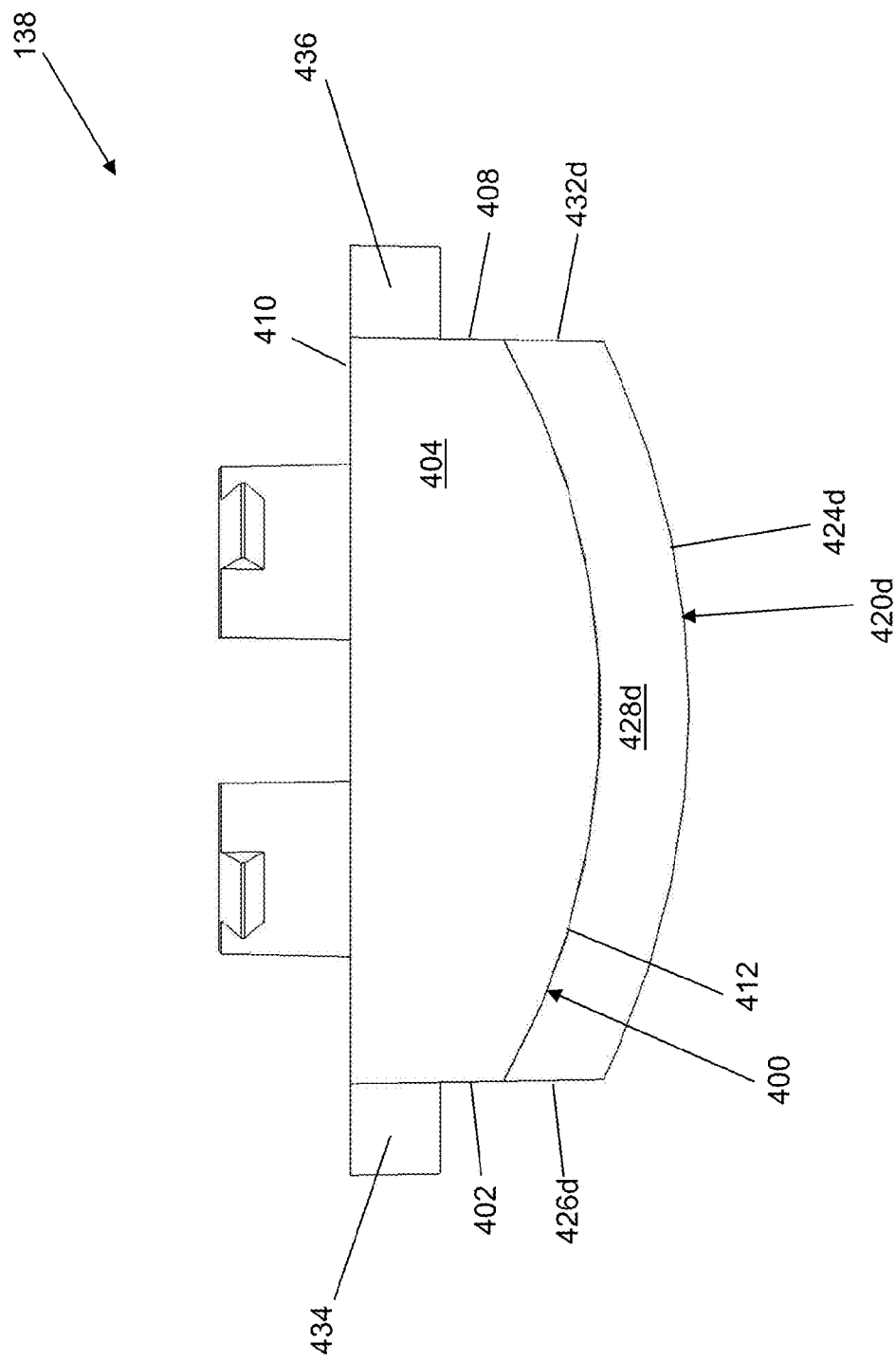
FIG. 4D depicts a right side view of the adapter of FIG. 4A.
Figure 4E:
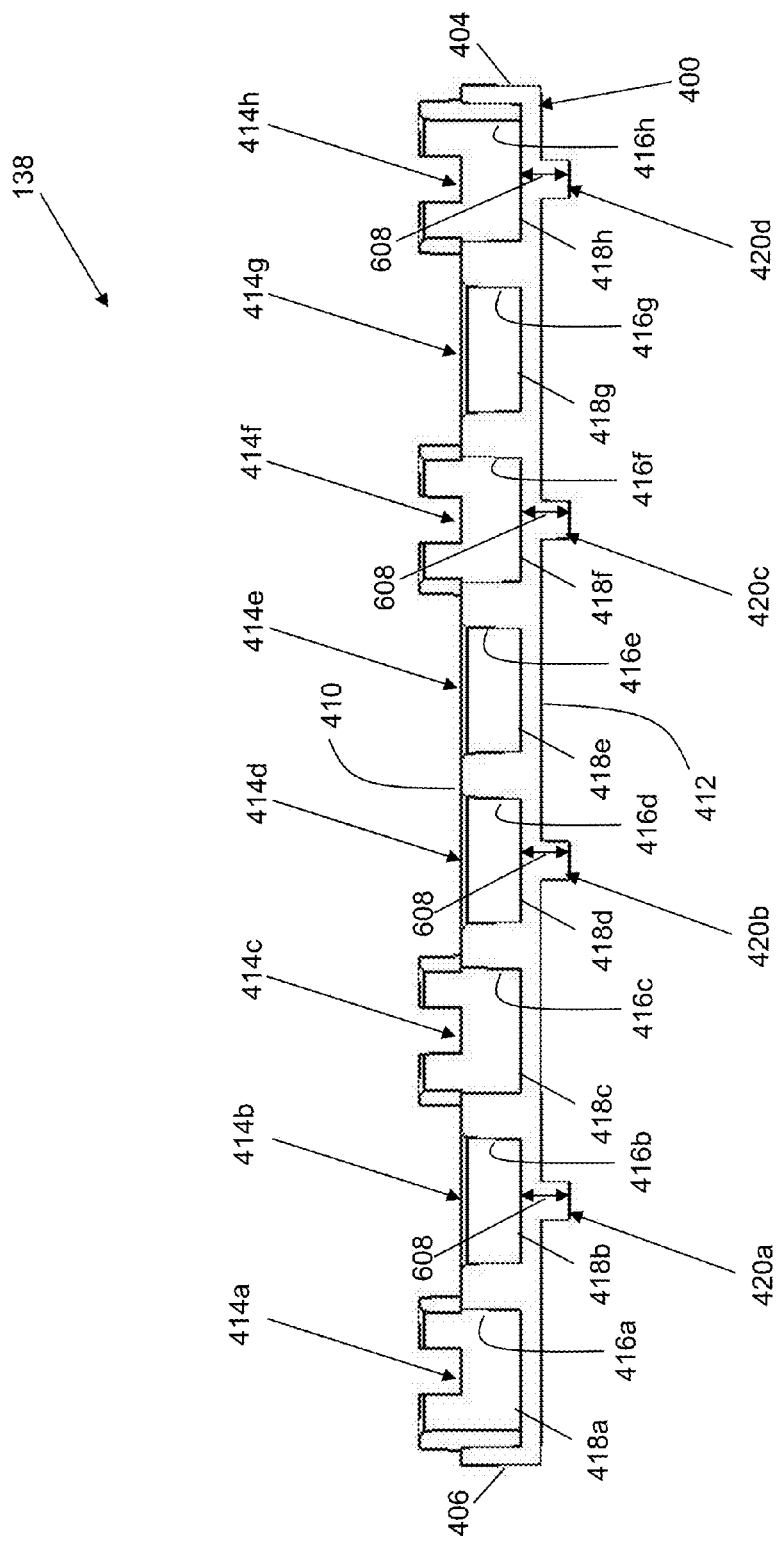
FIG. 4E depicts a front, cross-sectional view of the adapter of FIG. 4A.
Figure 5:
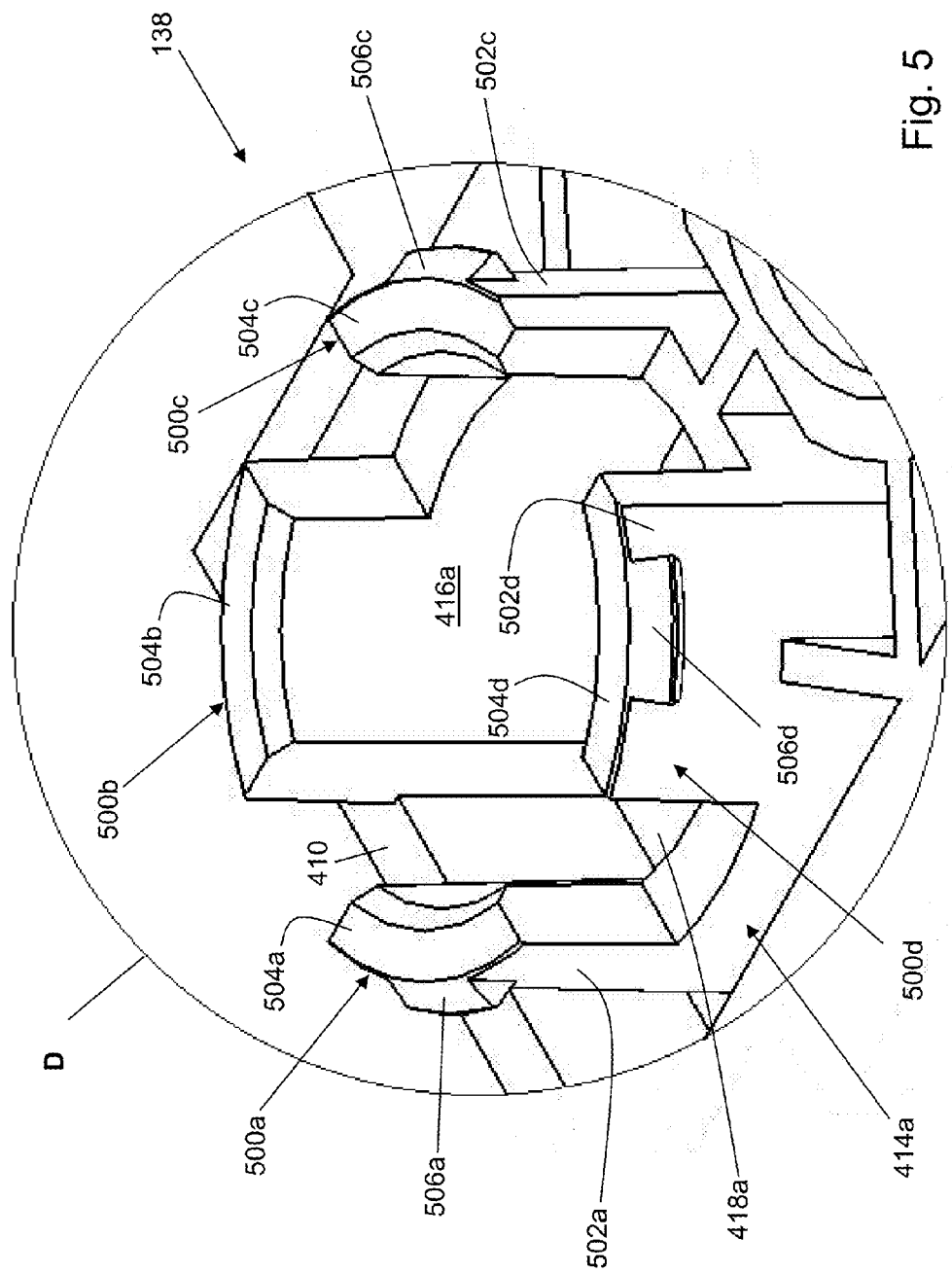
FIG. 5 depicts an enlarged view of a portion of adapter of FIG. 4A.
Figure 6:
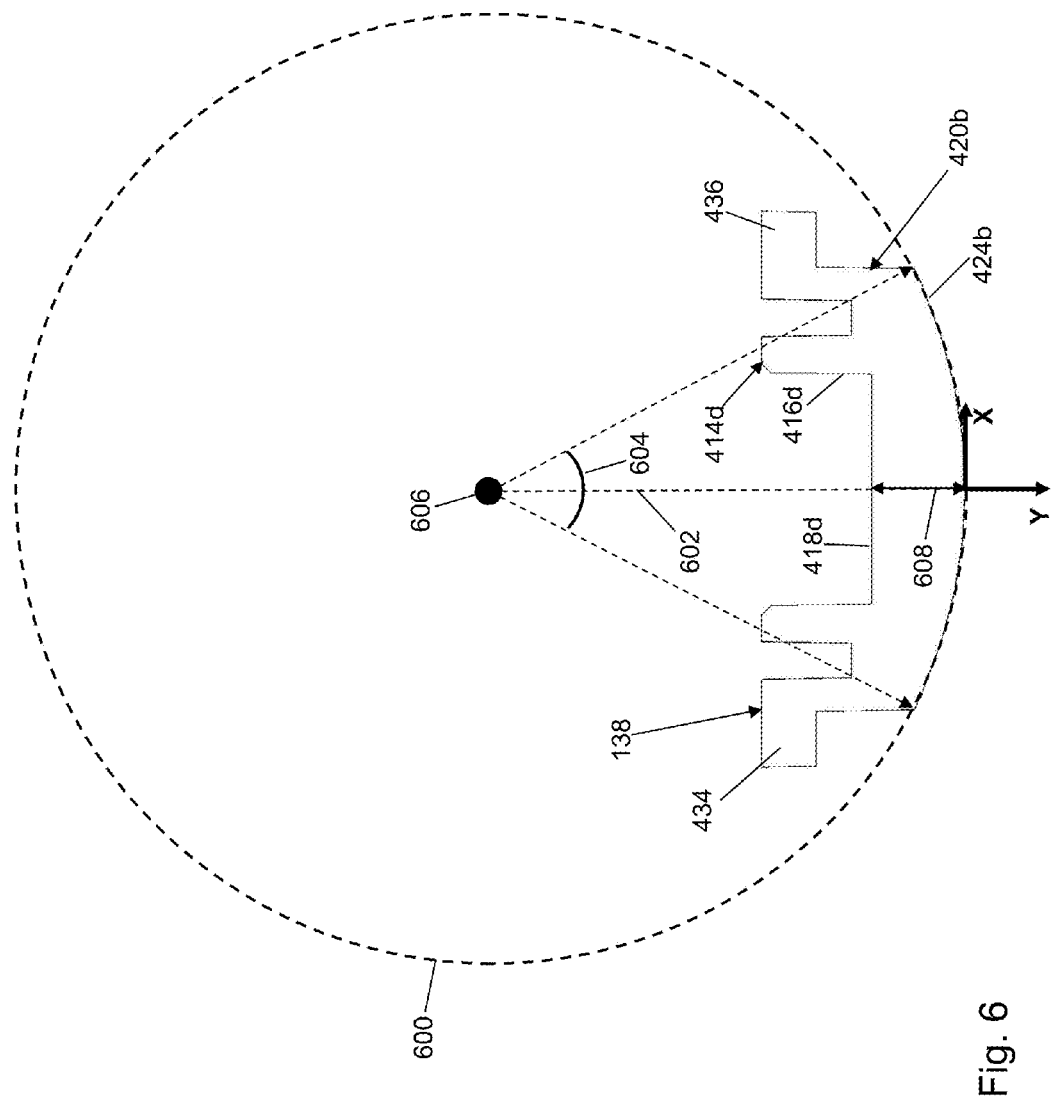
FIG. 6 depicts a cross-sectional view of the adapter of FIG. 4A.

With reference to FIGS. 4A-D, FIG. 5, and FIG. 6, views of adapter 138 are shown. With reference to FIG. 4A, a top, perspective view of adapter 138 is shown. With reference to FIG. 4B, a bottom, perspective view of adapter 138 is shown (i.e., in which adapter 138 has been rotated 180° about axis C). With reference to FIG. 4C, a front view of adapter 138 is shown. With reference to FIG. 4D, a right side view of adapter 138 is shown. With reference to FIG. 4E, a front, cross-sectional view of adapter 138 is shown, taken along section C-C. With reference to FIG. 5, an enlarged view of section D of FIG. 4A is shown. With reference to FIG. 6, a cross-sectional view of FIG. 4B is shown, taken along a plane containing XY axes 401. In FIG. 6, adapter 138 has been rotated 180° from the orientation shown in FIG. 4B.

Adapter 138 is configured to provide an interface between the plurality of magnets 166 mounted to sliding head 104 of sample processing system 100 and liquid in the wells of sample plate 106. Adapter 138 may include an adapter plate 400 that includes a top surface 410, a bottom surface 412, a front wall 402, a right side wall 404, a left side wall 406, and a back wall 408. Walls 402, 404, 406, 408 extend between top surface 410 and bottom surface 412 of adapter plate 400. Top surface 410 of adapter plate 400 may form part of a mounting surface of adapter 138 configured to mount to the plurality of magnets 166a-d and to bottom plate 300 of inner housing 134. Bottom surface 412 of adapter plate 400 may form part of a collection surface of adapter 138 configured to collect a plurality of magnetic particles (e.g., paramagnetic beads) from liquid contained in sample plate 106 and to hold the plurality of magnetic particles as adapter 138 translates over sample plate 106.

Adapter 138 may be configured to mount to the plurality of magnets 166 of sliding head 104. Various mounting configurations may be used. As shown in the illustrative embodiment, adapter plate 400 may include a plurality of recesses 414a-h extending from top surface 410 of adapter plate 400 towards bottom surface 412. Each recess of the plurality of recesses 414a-h may correspond to a respective recess of the plurality of recesses 308a-h of bottom plate 300 of inner housing 134. Each recess of the plurality of recesses 414a-h has side walls 416a-h and a bottom surface 418a-h that define an opening.

The size of each opening of each recess 414a-h may vary. The opening of each recess 414a-h may be sized and shaped to accommodate an end of first or second rigid members 162a and 162b or an end of one of the plurality of magnets 166a-d. In the illustrative embodiment, when adapter 138 is mounted to inner housing 134 of sliding head 104, an end of magnet 166a rests on bottom surface 418b of recess 414b. (See also FIG. 1D.) An end of magnet 166b rests on bottom surface 418d of recess 414d. An end of magnet 166c rests on bottom surface 418f of recess 414f. An end of magnet 166d rests on bottom surface 418h of recess 414h. As such, recesses 414b, 414d, 414f, and 414h are configured as magnet mounting recesses. Similarly, when first and second rigid members 162a and 162b are moved downwardly, an end of first rigid member 162a contacts bottom surface 418a of recess 414a, and an end of second rigid member 162b contacts bottom surface 418g of recess 414g. As such, recesses 414a and 414g are configured as rigid member receiving recesses. Recesses 414c and 414e may be blank recesses which neither mount nor receive a magnet or rigid member.

The size of each opening of each recesses 414a-h may also depend upon the dimensions of the wells of sample plate 106. The distance across opposing sides of each opening of each recess 414a-h may be approximately the same as the distance across opposing sides of the wells of sample plate 106. The distance across opposing sides of each opening of each recess 414a-h may be referred to as the width or diameter of each recess 414a-h.

Similarly, the shape of each opening of each recess 414a-h may vary. In the illustrative embodiment, each opening of each recess 414a-h has a cylindrical shape. However, other shapes, e.g., cubes, may be used. Adapter 138 may include various numbers of recesses, depending upon the number of magnets in sample processing system 100 and the number of mounting points of adapter 138 to bottom plate 300 of inner housing 134.

Adapter 138 may be configured to mount to bottom plate 300 of inner housing 134 of sliding head 104. Various mounting configurations may be used. As shown in the illustrative embodiment, adapter plate 400 may be configured to snap fasten to bottom plate 300 of inner housing 134.

With reference to FIG. 5, an enlarged view of recess 414a of FIG. 4A is shown. Side walls 416a extend above top surface 410 of adapter 138. Notches may be formed in side walls 416a to form a plurality of projections 500a-d configured to fit into recess 308a of bottom plate 300 of inner housing 134. Each projection 500a-d has an outer surface 502a-d (outer surface 502b is not shown) and a top end 504a-d. Each projection 500a-d may have a tab 506a-d (tab 506b is not shown) mounted to extend outward from each respective outer surface 502a-d near each respective top end 504a-d. Tabs 506a-d may be configured to fit into groove 316a of corresponding recess 308a of bottom plate 300 of inner housing 134. As shown in FIG. 4, recesses 414c, 414f, and 414h of adapter plate 400 may be configured similar to recess 414a. As such, recesses 414c, 414f, and 414h are configured to snap fasten to corresponding recesses 308a, 308c, 308f, and 308h of bottom plate 300 of inner housing 134. As shown in the illustrative embodiment, tabs 506a-d span only a portion of each respective projection 500a-d. However, in other embodiments, tabs may extend completely across each respective projection 500a-d. The width of the notches, i.e., the distance between projections may be selected to provide a selected rigidity.

The snap fastening configuration illustrated in FIGS. 4 and 5 allows adapter 138 to be quickly and easily attached to and detached from sliding head 104. In addition, the snap fastening configuration ensures that adapter 138 is mounted approximately level with respect to sample plate 106 and remains approximately level as adapter 138 translates over sample plate 106.

Adapter 138 may be configured to partially protrude into liquid contained in the wells of sample plate 106 as adapter 138 translates over sample plate 106 to facilitate the collection of the magnetic particles. Once the magnetic particles are bound to adapter 138, such protrusion also facilitates the immersion of the magnetic particles into liquid contained in other wells of sample plate 106. Various configurations may be used. In the illustrative embodiment, adapter plate 400 may include a plurality of ridges 420a-d, each ridge 420a-d extending from bottom surface 412 of adapter plate 400 away from top surface 410 and towards underlying sample plate 106. (See also FIG. 1D). Adapter plate 400 may not include any of the plurality of ridges 420a-d. Each ridge 420a-d may be aligned approximately parallel to each other and to a translation axis 422 defining the direction of translation of adapter 138. Each ridge 420a-d may be approximately centered below a corresponding magnet mounting recess 414b, 414d, 414f, and 414h of adapter plate 400. As such, when adapter 138 is mounted to the plurality of magnets 166a-d, each ridge 420a-d is approximately centered below a corresponding magnet 166a-d. Adapter 138 may include various numbers of ridges, depending upon the number of magnets in sample processing system 100.

In the illustrative embodiment, adapter plate 400 may include a plurality of curved surfaces 452a-d extending between each ridge 420a-d. In the illustrative embodiment of FIG. 4B, the curved surfaces 452a-d extend continuously an entire length of bottom surface 412 between right side wall 404 and left side wall 406 such that the plurality of ridges 420a-d extend from the curved surfaces 452a-d that comprise bottom surface 412. In alternative embodiments, the curved surfaces 452a-d may extend along only a portion of the length of bottom surface 412 between right side wall 404 and left side wall 406, and the curved surfaces 452a-d may not be continuous between right side wall 404 and left side wall 406. In alternative embodiments, the curved surfaces 452a-d may not be included. In alternative embodiments, either of the curved surfaces 452a-d or of the bottom surfaces 424a-d of ridges 420a-d may not be curved continuously between front wall 402 to back wall 408 of adapter plate 400. Instead, a leading edge and a trailing edge of the curved surfaces 452a-d or of the bottom surfaces 424a-d of ridges 420a-d may be curved in the direction from front wall 402 to back wall 408 of adapter plate 400. The plurality of particles 224 may attach to the portions of the curved surfaces 452a-d or to the portions of the bottom surfaces 424a-d of ridges 420a-d that are curved.

Ridges 420a-d may assume a variety of shapes. As shown in the illustrative embodiment, ridges 420a-d each have a bottom surface 424a-d, a front wall 426a-d, a right side wall 428a-d, a left side wall 430a-d, and a back wall 432a-d, the walls extending between bottom surfaces 424a-d and bottom surface 412 of adapter plate 400.

Bottom surfaces 424a-d of ridges 420a-d may be curved in one or more directions. As shown in the illustrative embodiment, each bottom surface 424a-d may be curved along a direction parallel to translational axis 422. The plurality of curved surfaces 452a-d are curved in the same manner as each bottom surface 424a-d. With reference to FIG. 4B, an axis X defines the direction of curvature of bottom surface 424b of ridge 420b and an axis Y is perpendicular to axis X and in-out of a plane defined through adapter plate 400.

With reference to FIG. 6, a cross-sectional view of adapter 138 taken along a plane containing both axes X and Y is shown. The cross-sectional view is rotated by 180° to correspond to the orientation of adapter 138 when mounted to sliding head 104 (as shown in FIG. 1D). Bottom surface 424b of ridge 420b forms a circular arc of a circle 600 having a radius 602. A radius of curvature is a radius of a circle that best fits a normal section. Bottom surface 424b of ridge 420b is the circumference of circle 600 formed by an angle 604 and has a radius of curvature equal to radius 602. The radius of curvature may be selected to maximize recovery of the magnetic particles while minimizing the carryover of liquid between wells of sample plate 106 (to avoid contamination of the liquid in the wells). In some embodiments, the radius of curvature is in the range of approximately 0.4 inches to approximately 0.7 inches. A center 606 of circle 600 forming bottom surface 424b is located above bottom surface 424b in a direction of the interior of inner housing 134. Thus, the curvature of bottom surface 424b is concave relative to inner housing 134. With respect to sample plate 106, over which adapter 138 may be mounted, the curvature of bottom surface 424b is convex. With respect to inner housing 134 to which adapter 138 may be mounted, the curvature of bottom surface 424b is concave. Bottom surfaces 424a, 424c, and 424d of ridges 420a, 420c, and 420d may be configured similarly to bottom surface 424b of ridge 420b. With reference to FIGS. 4B and 4D, bottom surface 412 of adapter plate 400 may also be curved though bottom surface 412 of adapter plate 400 may also have another shape such as flat. As shown in the illustrative embodiment, the direction of curvature (from front to back), radius of curvature, and type of curvature (i.e., convex or concave) of bottom surface 412 may be approximately the same as the direction of curvature, radius of curvature, and type of curvature of bottom surfaces 424a-d of ridges 420a-d. As an example, the radius of curvature may be less than ~800 microns.

Ridges 420a-d may have a variety of dimensions. The dimensions may be selected to maximize recovery and retention of the magnetic particles while minimizing a disturbance of the liquid in the wells of sample plate 106 (to avoid spillage or wicking of liquid outside the wells of sample plate 106). The dimensions may also depend upon the dimensions of the wells of sample plate 106. The dimension between respective right and left side walls 428a-d, 430a-d of ridges 420a-d may be referred to as the width of each ridge 420a-d. The width of each ridge 420a-d may be smaller than the distance across opposing sides of the wells (e.g., wells 712a-d with reference to FIG. 7) in sample plate 106. (See also FIG. 1D.) The dimension between respective front and back walls, 426a-d, 432a, and 423d of ridges 420a-d may be referred to as the length of each ridge 420a-d. Each ridge 420a-d may be sufficiently long to extend across bottom surface 412 of adapter plate 400 from front wall 402 to back wall 408 of adapter plate 400. The dimension between bottom surface 412 of adapter plate 400 and respective bottom surfaces 424a-d of ridges 420a-d may be referred to as the height of each ridge 420a-d. The height of each ridge 420a-d may be sufficient to protrude a selected distance into liquid contained in sample plate 106 when adapter 138 is mounted to sliding head 104.

With reference to FIG. 6, a thickness 608 (the dimension between bottom surface 418d of magnet mounting recess 414d and bottom surface 424b of ridge 420b) may be selected to reduce a distance between magnet 166b mounted in magnet mounting recess 414d and the liquid contacting bottom surface 424b of ridge 420b possibly based on a magnetic force of magnet 166b. This facilitates the recovery and retention of the magnetic particles from the liquid contained in the wells of sample plate 106. With reference to FIG. 4E, thickness t may be similarly selected for each other magnet mounting recess 414b, 414f, and 414h and its corresponding ridge 420a, 420c, and 420d.

With reference to FIGS. 4A and 4B, adapter 138 may include a first rail 434 extending from front wall 402 of adapter plate 400 and a second rail 436 extending from back wall 408 of adapter plate 400. First rail 434 and second rail 436 enable adapter 138 to sweep through the meniscus of the liquid above the surface of sample plate 106 and prevent carryover of the liquid from well to well.

The components of adapter 138 may be molded as a single piece. The components of adapter 138 may be formed from a variety of materials, e.g., plastics, having sufficient strength and biocompatibility. The type of material may be selected to have sufficient rigidity to ensure consistent and reproducible positioning of adapter 138 above sample plate 106. The type of material may be selected to have a selected hydrophobicity and low adsorption of biomolecules. Alternatively, the selected material may be coated with a material having a selected hydrophobicity. Surfaces of adapter 138, e.g., bottom surface 412, ridges 420a-d, etc., may be made sufficiently smooth (e.g., A3+ surface finish) to maximize recovery of the magnetic particles while minimizing the carryover of liquid between wells of sample plate 106 (to avoid contamination of the liquid in the wells).

Figure 7A:
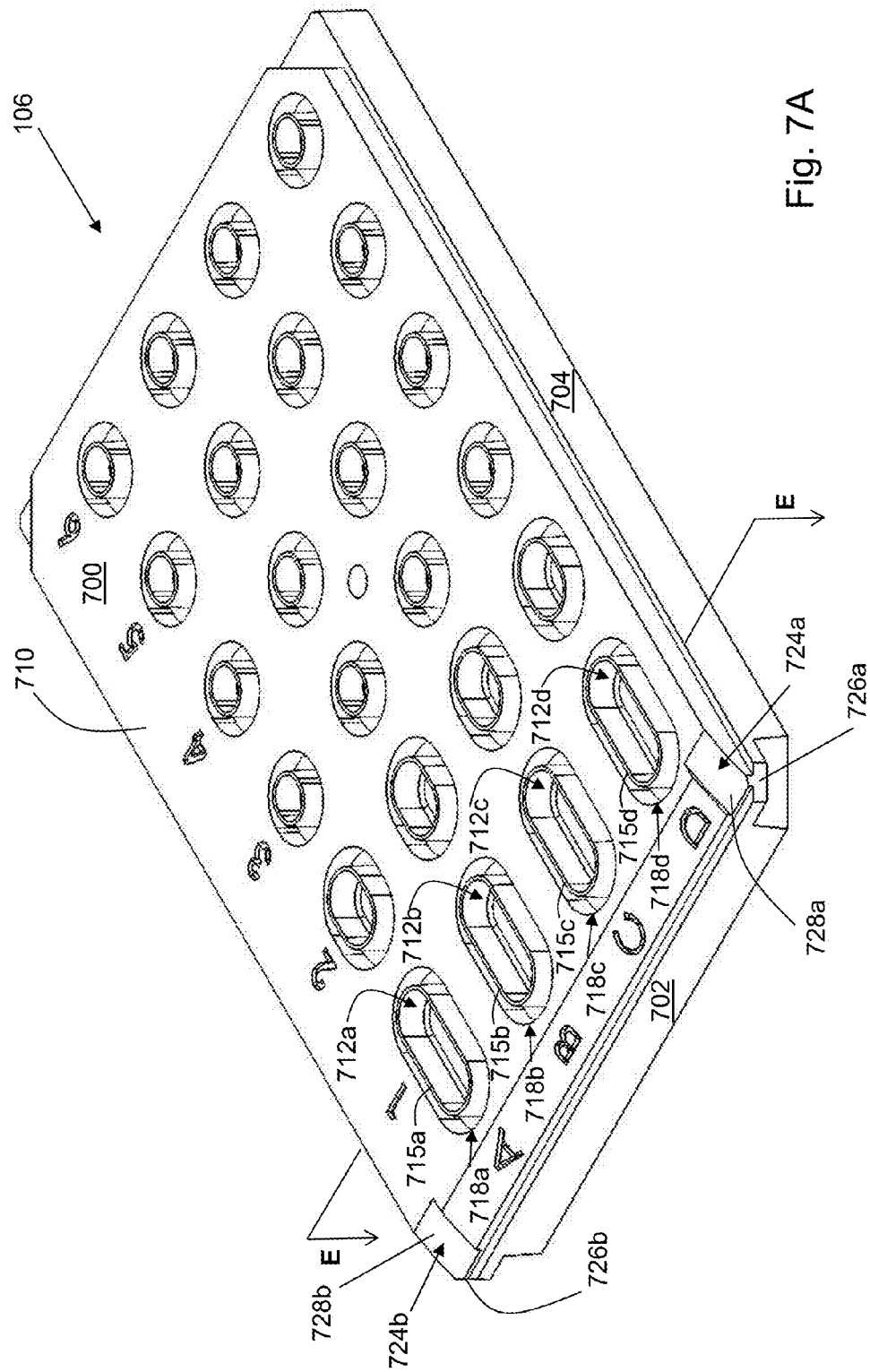
FIG. 7A depicts a perspective view of a sample plate of the sample processing system of FIG. 1A.
Figure 7B:
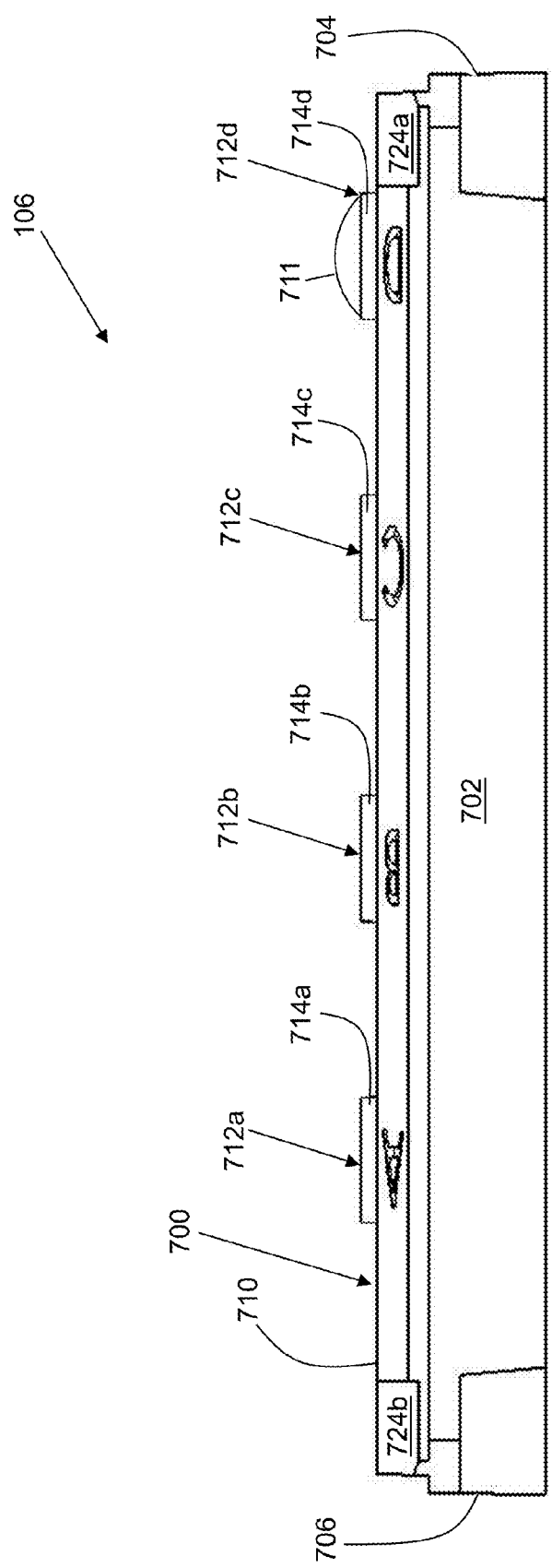
FIG. 7B depicts a front view of the sample plate of FIG. 7A.
Figure 7C:
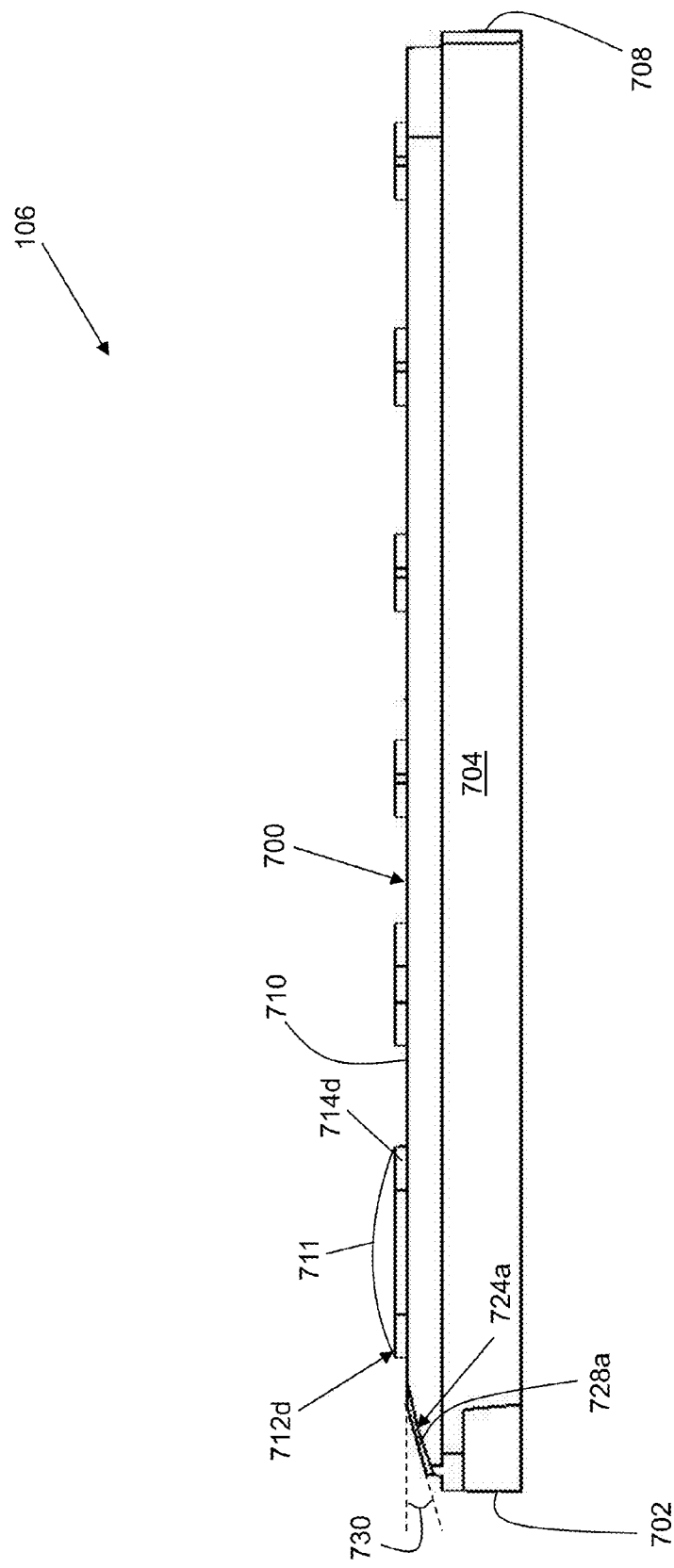
FIG. 7C depicts a right side view of the sample plate of FIG. 7A.
Figure 7D:
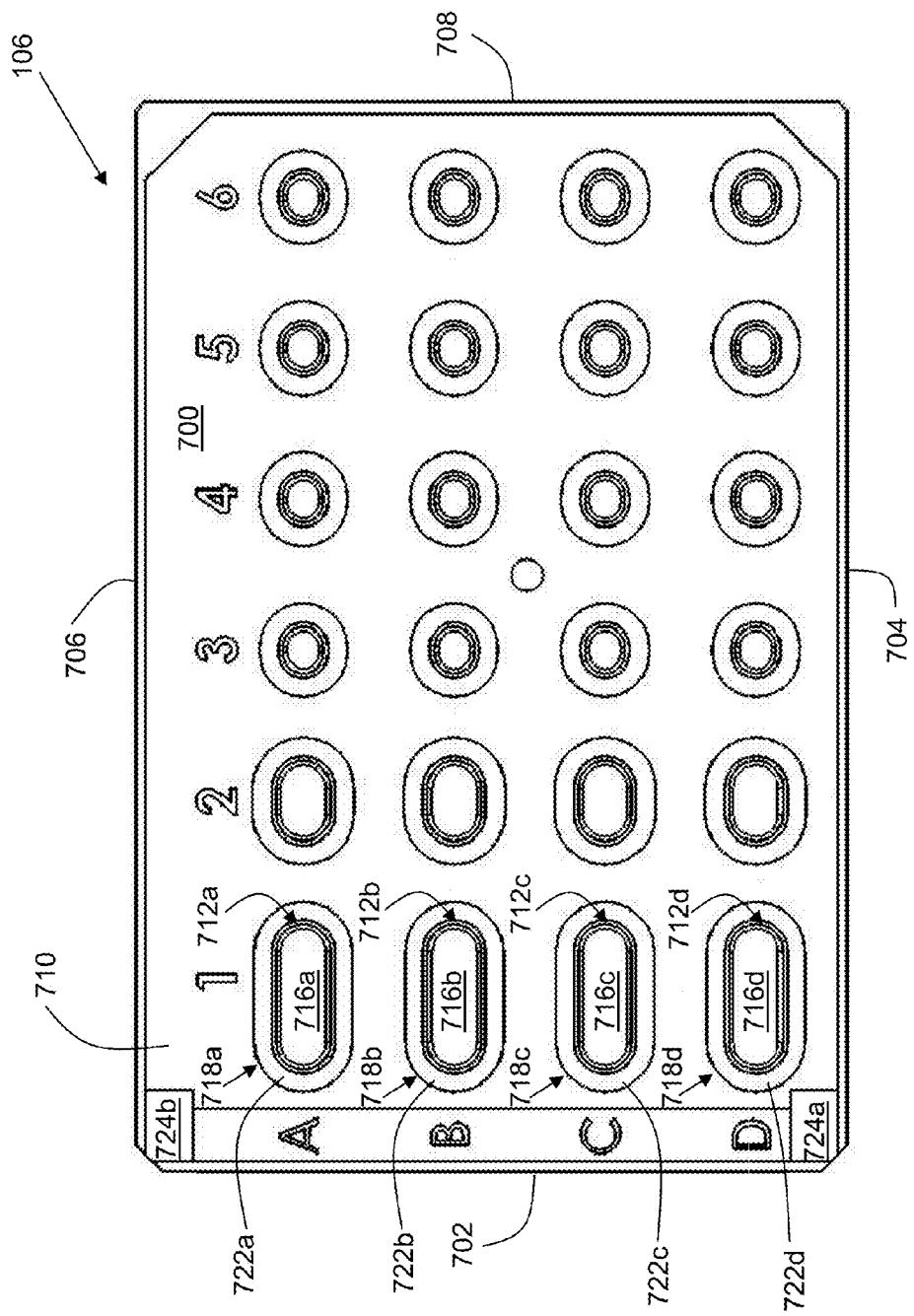
FIG. 7D depicts a top view of the sample plate of FIG. 7A.
Figure 7E:
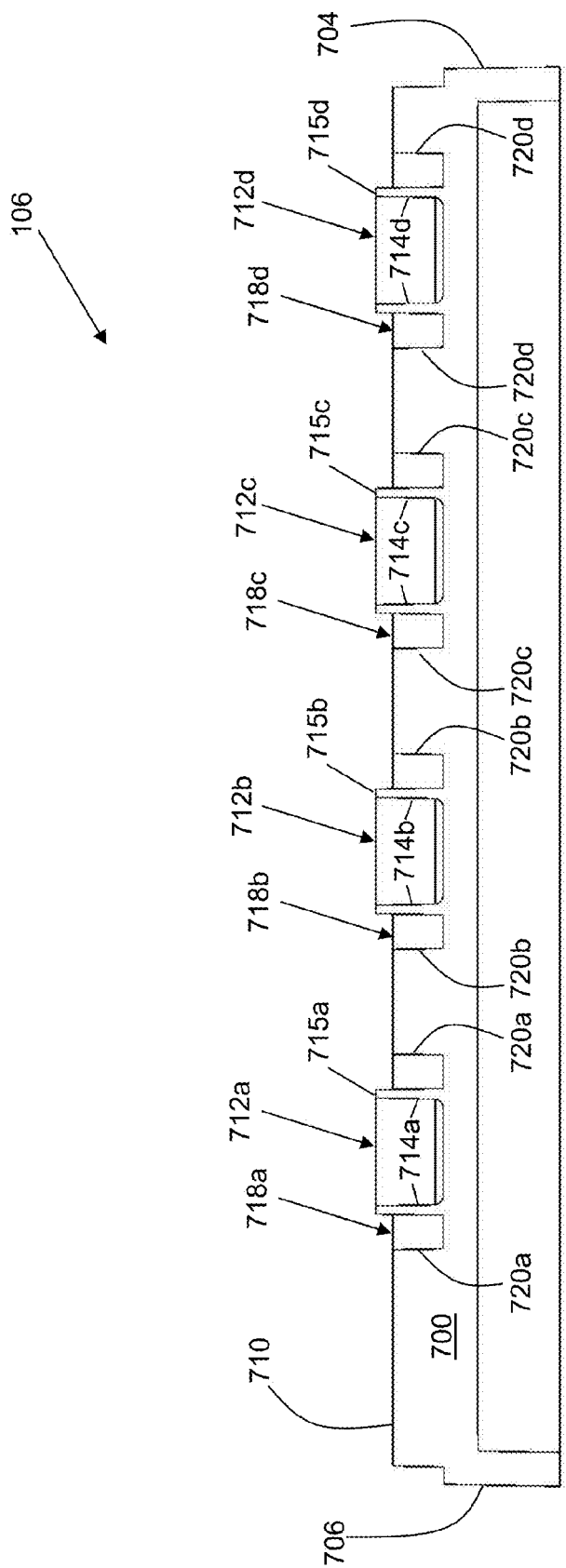
FIG. 7E depicts a front, cross-sectional view of the sample plate of FIG. 7A.

With reference to FIGS. 7A-E, views of sample plate 106 are shown. With reference to FIG. 7A, a perspective view of sample plate 106 is shown. With reference to FIG. 7B, a front view of sample plate 106 is shown. With reference to FIG. 7C, a right side view of sample plate 106 is shown. With reference to FIG. 7D, a top view of sample plate 106 is shown. With reference to FIG. 7E, a front, cross-sectional view of sample plate 106 is shown, taken along section E-E.

Sample plate 106 is configured to hold a plurality of liquid samples (e.g., liquid mixtures including target analytes bound to magnetic particles) and other liquid mixtures (e.g., liquid mixtures including processing reagents, buffers, wash solvents, etc.). Sample plate 106 may include a base plate 700, a front wall 702, a right side wall 704, a left side wall 706, and a back wall 708. Base plate 700 includes a top surface 710. Base plate 700 may include a plurality of wells, including wells 712a-d, formed in top surface 710. The plurality of wells may be arranged in a grid pattern in top surface 710, the grid pattern including rows of wells (rows are labeled A-D for illustration) and columns of wells (columns are labeled 1-6 for illustration). Sample plate 106 may include various numbers of wells, depending upon the number of liquid samples to be processed and the number of processing steps to be performed by sample processing system 100.

Each well 712a-d is configured to hold liquid. Each well 712a-d has side walls 714a-d and a bottom surface 716a-d defining an interior of each well 712a-d. Side walls 714a-d may extend both below and above a plane of top surface 710 of base plate 700. As exemplified in FIG. 7B, C, this allows a meniscus 711 of liquid contained in each well 712a-d to protrude above top surface 710 of base plate 700. The amount that side walls 714a-d extend above top surface 710 may be selected to provide a selected height of meniscus 711 above top surface 710. In some embodiments, side walls 714a-d extend above top surface by at least about 0.01 inches, at least about 0.2 inches, at least about 0.04 inches, etc. Side walls 714a-d each have a top edge 715a-d. Top edges 715a-d may be made sufficiently sharp to promote the formation of meniscus 711. For example, top edge 715a-d may be angled between 45 and 125 degrees.

Interiors of each well 712a-d may also be otherwise sized and shaped to accommodate a selected volume of liquid (e.g., 1 mL, 0.5 mL, 0.25 mL, 0.1 mL, etc.). Each well 712a-d may assume a variety of shapes as defined by side walls 714a-d, e.g., circular, elliptical, polygonal such as square rectangular, triangular, etc. Each well in the plurality of wells of sample plate 106 may be configured similarly to wells 712a-d. However, the shapes and sizes of the wells of the plurality of wells of sample plate 106 may differ from one another. In this way, sample plate 106 can accommodate different volumes of liquid. In the illustrative embodiment, wells 712a-d in column 1 each have an elliptical shape and are sized to accommodate a volume of about 0.5 mL. The wells are designed to pin the meniscus of the liquid (to the upper edge of the well). The wells in column 2 also have an elliptical shape, but are sized to accommodate a smaller volume of about 0.25 mL. The remaining wells in columns 3, 4 and 5 each have a circular shape and are sized to accommodate an even smaller volume of about 0.10 mL.

Sample plate 106 may be configured to reduce cross-contamination of liquid contained in the wells of the plurality of wells. Base plate 700 may include a plurality of reservoirs, including reservoirs 718a-d, formed in top surface 710, each reservoir surrounding a corresponding well in the plurality of wells. Each reservoir 718a-d is configured to capture liquid spilling or wicking from corresponding wells 712a-d. Such spilling or wicking may occur when sample plate 106 is agitated or when the plurality of ridges 420a-d of adapter 138 translates through liquid contained in wells 712a-d, thereby disturbing liquid contained therein. Each reservoir 718a-d has side walls 720a-d and a bottom surface 722a-d. Each reservoir 718a-d shares a respective side wall 714a-d of one of the corresponding wells 712a-d which it surrounds. Side walls 720a-d and 714a-d and bottom surface 722a-d define an interior. Interiors of each reservoir 718a-d may be sized to accommodate a selected volume of spilled or wicked liquid. Each reservoir 718a-d may assume a variety of shapes, as determined by side walls 720a-d and 714a-d. Each reservoir in the plurality of reservoirs may be configured similarly to reservoirs 718*a-d*. However, the shapes of the reservoirs in the plurality of reservoirs of sample plate 106 may differ from one another. In the illustrative embodiment, reservoirs 718*a-d* in column 1 each have an elliptical shape. The reservoirs in column 2 each have an elliptical shape. The remaining reservoirs in columns 3, 4 and 5 each have a circular shape.

Sample plate 106 may include a first ramp 724*a* formed in top surface 710 at a right corner 726*a* of base plate 700 and a second ramp 724*b* formed in top surface 710 at a left corner 726*b* of base plate 700. First and second ramps 724*a*, 724*b* each have a top surface 728*a*, 728*b*, respectively. The slope of first ramp 724*a* may be characterized by an angle 730 between the plane defined by top surface 710 of base plate 700 and the plane defined by top surface 728*a* of first ramp 724*a*. Angle 730 may be selected to facilitate the initial positioning of the sliding head 104 over the sample plate 106. Second ramp 724*b* may be similarly configured.

The components of sample plate 106 may be molded as a single piece. The components of sample plate 106 may be formed from a variety of materials, e.g., plastics, having sufficient strength, rigidity and biocompatibility. The type of material may be selected to have a selected hydrophobicity. Alternatively, the selected material may be coated with a material having a selected hydrophobicity. The use of hydrophobic materials/coatings may promote the formation of meniscus 711. Surfaces of the plurality of wells of sample plate 106 may be made sufficiently smooth (e.g., A3+ surface finish) to facilitate insertion and removal of liquid from the wells. A bottom of the wells may be curved to prevent trapping of the plurality of particles 224 in a corner.

As shown referring to FIG. 1D, each ridge 420*a-d* may be approximately centered below a corresponding magnet mounting recess 414*b*, 414*d*, 414*f*, and 414*h* of adapter plate 400 and approximately over the centers of wells 712*a-d* of sample plate 106 when translating over sample plate 106. In an alternative embodiment as shown referring to FIG. 8, adapter 138 may be rotated 180 degrees such that each of the plurality of curved surfaces 452*a-d* is approximately centered below a corresponding magnet 166*a-d* and approximately centered above the centers of wells 712*a-d* of sample plate 106 when translating over sample plate 106. A height of each ridge 420*a-d* may be selected to provide contact between the plurality of curved surfaces 452*a-d* and the meniscus of the samples.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more". Still further, the use of "and" or "or" is intended to include "and/or" unless specifically indicated otherwise.

The foregoing description of illustrative embodiments of the disclosure has been presented for purposes of illustration and of description. It is not intended to be exhaustive or to limit the disclosure to the precise form disclosed, and modifications and variations are possible in light of the above teachings or may be acquired from practice of the disclosure. The embodiments were chosen and described in order to explain the principles of the disclosure and as practical applications of the disclosure to enable one skilled in the art to utilize the disclosure in various embodiments and with various modifications as suited to the particular use contemplated. It is intended that the scope of the disclosure be defined by the claims appended hereto and their equivalents

What is claimed is:

1. A sample processing system comprising:
a first base comprising an upper surface;
a sample plate mounted to the upper surface, the sample plate comprising a top surface;
   a plurality of wells mounted to the top surface, each well comprising a well bottom surface and a well wall extending up from the well bottom surface; and
   a plurality of reservoirs mounted to the top surface, each reservoir comprising a reservoir bottom surface, a reservoir wall extending from a first side of the reservoir bottom surface, and the well wall extending from a second side of the reservoir bottom surface, wherein each reservoir of the plurality of reservoirs surrounds a corresponding well of the plurality of wells; and
a sliding head mounted to the first base to translate over the sample plate in a translation direction, the sliding head comprising
   a housing comprising a second base,
   a magnet mounted in the housing to extend through the second base, and
   an adapter mounted to the second base.

2. The sample processing system of claim 1, wherein the well wall extends above the top surface an amount to provide a selected height of a meniscus of a liquid contained by the well wall above the top surface.

3. The sample processing system of claim 2, wherein the well wall extends at least about 0.02 inches above the top surface.

4. The sample processing system of claim 2, wherein the well wall extends below the top surface.

5. The sample processing system of claim 2, wherein the reservoir wall extends below the top surface, but not above the top surface.

6. The sample processing system of claim 5, wherein the well wall extends below the top surface.

7. The sample processing system of claim 2, wherein the well wall extends from about 0.01 inches to about 0.04 inches above the top surface.

8. The sample processing system of claim 1, wherein the plurality of wells comprises at least one well having an elliptical shape.

9. The sample processing system of claim 1, wherein the plurality of wells comprises a first well having a first shape and a second well having a second shape, wherein the first shape is different from the second shape.

10. The sample processing system of claim 9, wherein the first shape is elliptical and the second shape is circular.

11. The sample processing system of claim 1, wherein the plurality of wells comprises a first well configured to accommodate a first volume of liquid and a second well configured to accommodate a second volume of liquid, wherein the first volume is different from the second volume.

12. The sample processing system of claim 11, wherein the plurality of wells further comprises a third well configured to accommodate a third volume of liquid, wherein the third volume of liquid is different from the first and second volumes.

13. The sample processing system of claim 1, wherein the plurality of wells and the plurality of reservoirs are arranged in a grid pattern comprised of a plurality of rows and a plurality of columns.

14. The sample processing system of claim 13, wherein the wells in a first column each have a first shape and the wells in a second column each have a second shape, wherein the first shape is different from the second shape.

15. The sample processing system of claim 14, wherein the first shape is elliptical and the second shape is circular.

16. The sample processing system of claim 13, wherein the wells in a first column each have an elliptical shape and are configured to accommodate a first volume of liquid and the wells in a second column each have an elliptical shape and are configured to accommodate a second volume of liquid, wherein the first volume is different from the second volume.

17. The sample processing system of claim 16, wherein remaining wells of the plurality of wells each have a circular shape and are configured to accommodate a third volume of liquid, wherein the third volume of liquid is different from the first and second volumes.

18. The sample processing system of claim 1, wherein the well walls and the reservoir walls are approximately perpendicular to the top surface and the well bottom surfaces and the reservoir bottom surfaces are approximately parallel to the top surface.

19. The sample processing system of claim 18, wherein a corner defined by the intersection of the well wall and the well bottom surface is curved so as to prevent trapping of a plurality of magnetic particles in a liquid contained by the well wall in the corner.

20. The sample processing system of claim 1, wherein a top edge of the well walls opposite the well bottom surface has an angle between −45 degrees and +45 degrees relative to vertical to promote the formation of a meniscus of a liquid contained by the well walls.

21. The sample processing system of claim 1, wherein the adapter comprises a ridge mounted to extend from the adapter in a direction towards the sample plate when the sample plate is mounted to the upper surface, wherein the ridge is curved and aligned with the plurality of wells when the sample plate is mounted to the upper surface.

22. The sample processing system of claim 1, further comprising a first ramp formed in the top surface at a first corner of the sample plate and a second ramp formed in the top surface at a second corner of the sample plate, wherein the first and second ramps are configured to facilitate the positioning of the sliding head of the sample processing system over the sample plate.

* * * * *